(12) United States Patent
Nieman et al.

(10) Patent No.: US 8,292,908 B2
(45) Date of Patent: Oct. 23, 2012

(54) ENDOSCOPIC CANNULATION APPARATUS AND METHOD

(75) Inventors: Timothy R. Nieman, North Salt Lake, UT (US); Scott D. Miles, Sandy, UT (US); Kent F. Beck, Layton, UT (US)

(73) Assignee: World Heart Corporation, Salt Lake City, UT (US)

( * ) Notice: Subject to any disclaimer, the term of this patent is extended or adjusted under 35 U.S.C. 154(b) by 1836 days.

(21) Appl. No.: 10/370,018

(22) Filed: Feb. 20, 2003

(65) Prior Publication Data
US 2003/0130668 A1  Jul. 10, 2003

Related U.S. Application Data

(63) Continuation-in-part of application No. 10/186,307, filed on Jun. 28, 2002.

(60) Provisional application No. 60/301,795, filed on Jun. 29, 2001.

(51) Int. Cl.
*A61B 17/22* (2006.01)
*A61M 29/00* (2006.01)

(52) U.S. Cl. ........ 606/159; 606/170; 606/180; 606/184; 606/191; 606/198; 604/22

(58) Field of Classification Search .................. 606/184, 606/159, 180, 170; 600/564, 566, 567
See application file for complete search history.

(56) References Cited

U.S. PATENT DOCUMENTS

| | | | |
|---|---|---|---|
| 3,552,712 A | 1/1971 | Whitlock | |
| 4,312,493 A | 1/1982 | Stauffer | |
| 4,524,802 A | 6/1985 | Lawrence et al. | |
| 4,610,664 A | 9/1986 | Harle | |
| 4,697,785 A | 10/1987 | Tuseth | |
| 4,718,634 A | 1/1988 | Bond | |
| 4,769,031 A | 9/1988 | McGough et al. | 623/1 |
| 4,794,928 A * | 1/1989 | Kletschka | 606/194 |
| 4,795,446 A | 1/1989 | Fecht et al. | |
| 5,041,131 A | 8/1991 | Nagase | |
| 5,290,306 A * | 3/1994 | Trotta et al. | 606/194 |
| 5,326,344 A | 7/1994 | Bramm et al. | 623/3 |
| 5,336,051 A | 8/1994 | Tamari | |
| 5,385,581 A | 1/1995 | Bramm et al. | 623/3 |
| 5,488,958 A * | 2/1996 | Topel et al. | 600/567 |
| 5,762,624 A | 6/1998 | Peters | |
| 5,814,005 A | 9/1998 | Barra et al. | 604/8 |
| 5,968,053 A | 10/1999 | Revelas | 606/108 |
| 6,033,427 A * | 3/2000 | Lee | 606/213 |
| 6,039,078 A | 3/2000 | Tamari | |
| 6,083,237 A * | 7/2000 | Huitema et al. | 600/567 |
| 6,266,550 B1 * | 7/2001 | Selmon et al. | 600/407 |

(Continued)

*Primary Examiner* — Tuan V Nguyen
(74) *Attorney, Agent, or Firm* — Holland & Hart LLP

(57) ABSTRACT

A method and apparatus for remotely cannulating a body part are disclosed. The apparatus is an endoscopic cannulation apparatus having a fluid stasis assembly and a coring assembly. The fluid stasis assembly allows for the penetration of the body part and deployment of an occlusive device to prevent the escape of fluid during the coring and cannulation of the body part. The cannulation assembly allows for the coring of the body part without the introduction of air bubbles or other embolic materials into the patient. The method of the invention provides for the remote coring and cannulation of a body part such as a heart, blood vessels, the stomach, intestines, and other body parts with a sealed apparatus that may be de-aired to lessen the risk of the introduction of emboli into a system.

66 Claims, 22 Drawing Sheets

U.S. PATENT DOCUMENTS

| | | | |
|---|---|---|---|
| 6,416,527 B1 * | 7/2002 | Berg et al. | 606/180 |
| 6,475,222 B1 * | 11/2002 | Berg et al. | 606/108 |
| 6,712,831 B1 * | 3/2004 | Kaplan et al. | 606/153 |
| 2002/0045846 A1 | 4/2002 | Kaplon et al. | 604/9 |

* cited by examiner

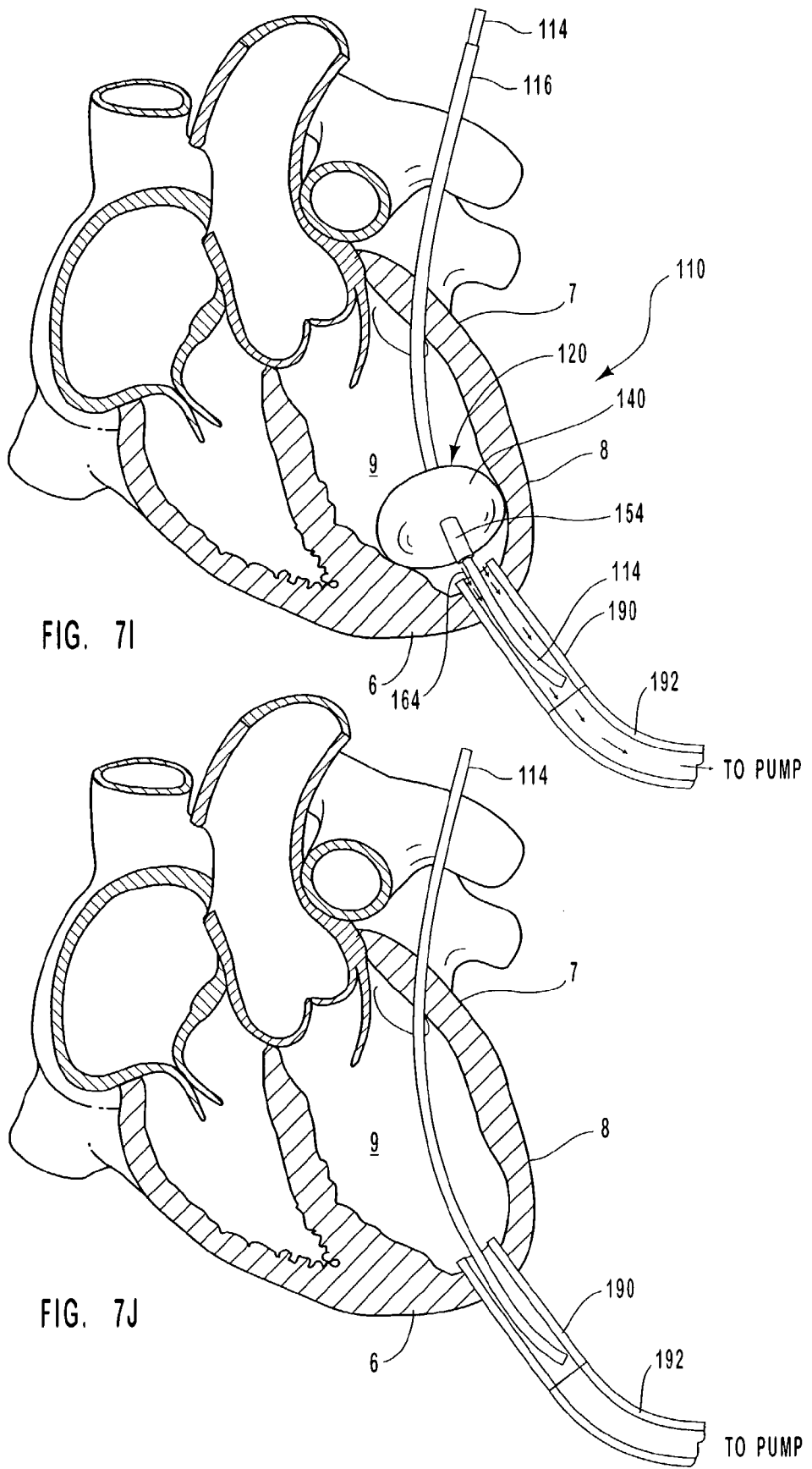

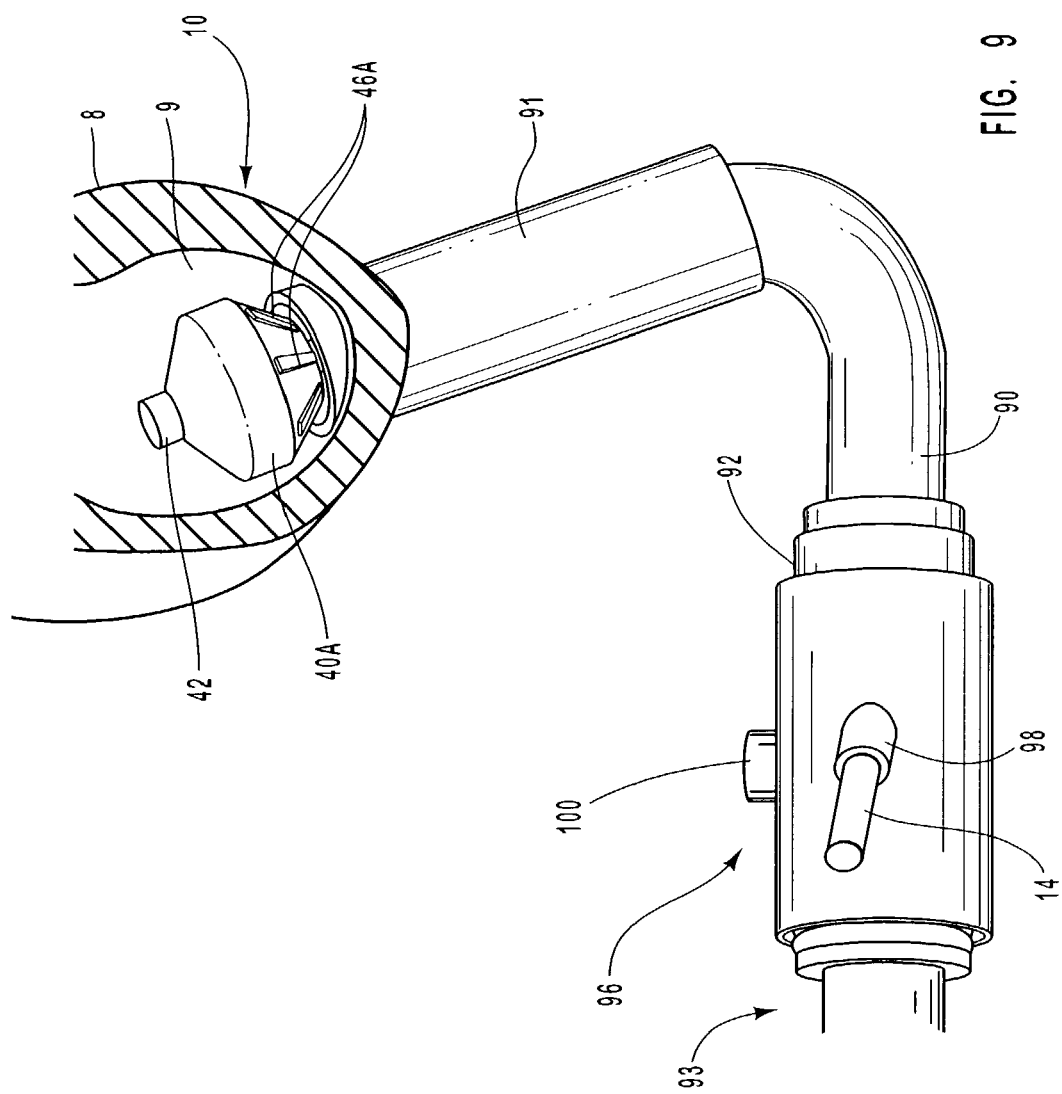

ENDOSCOPIC CANNULATION APPARATUS AND METHOD

RELATED APPLICATIONS

This application is a continuation-in-part of U.S. patent application Ser. No. 10/186,307, filed Jun. 28, 2002, entitled "Cannulation Apparatus and Method", which claims the benefit of U.S. Provisional Application Ser. No. 60/301,795, filed Jun. 29, 2001, entitled "Remote Cannulation Apparatus and Method." Both of these applications are incorporated herein by reference.

BACKGROUND OF THE INVENTION

1. Field of the Invention

The present invention relates to procedures and apparatus to assist in surgery which requires the penetration of a body part without permitting inflow or outflow of air, fluid, or other materials. More specifically, the present invention relates to methods and apparatus for remotely coring and cannulating a body part such as the heart, blood vessels, the stomach, intestines, and other body parts.

2. Description of Related Art

Historically, many treatments for severe forms of heart disease involved some form of open-heart surgery. Open-heart surgeries are historically costly, and generally require extended periods of convalescence. In addition, open-heart surgeries often require either large transfusions of blood to a patient, or the banking of the patient's blood in advance due to the significant blood loss often involved in the surgery.

Recently, in heart surgery and many other surgical procedures, less invasive surgical methods have been developed which require smaller incisions into a patient's chest cavity and result in less loss of blood. Such procedures often reduce the recovery time associated with a surgery, and may also improve the survival rate associated with the surgery.

One specific area of concern present in these and other procedures is the potential introduction of particles, such as air bubbles, clotted blood, or small pieces of tissue, into the bloodstream of the patient. Such debris may travel through the circulatory system of the patient and lodge in narrower vessels of tissues such as the brain, cutting off blood circulation. These "emboli" may cause severe complications, and even death.

Current procedures for heart surgeries including the implantation of left ventricular assist devices (LVAD), right ventricular assist devices (RVAD), total artificial hearts (TAH), as well as other devices, require major incursions into the patient's body and circulatory system. Generally, the patient's heart must be accessed through a large incision made in the patient's sternum. Such surgery is fraught with danger since it exposes the patient to a substantial risk of complications such as introduction of air into the circulatory system, bleeding, and infection. Such complications may result in serious patient injury or death.

Additionally, such implanted devices may require the insertion of a cannula in the heart to allow circulating blood to be channeled away from the heart. The implantation of a cannula requires that the heart be punctured or cored to allow placement of the cannula. This procedure, like the others mentioned above, has historically created a risk for patients. Thus, there is a need in the art for methods and apparatus for cannulating the heart and attaching a heart assist/replacement device that minimize the risk of introducing air into the patient's circulatory system, and reduce the high loss of blood also incident to such procedures.

In other medical procedures, organs such as the stomach, intestines, and blood vessels must be entered. As discussed with reference to heart-related procedures above, in many of these surgeries it is necessary to enter or exit other body parts without allowing fluid, air, or other materials to enter or exit the body part. Similarly, in such procedures it may be desirable to enter or exit the body part and install a cannula for further access. As with the heart-related surgeries discussed above, these surgeries have posed a serious risk to patients, and are also expensive and time-consuming.

Accordingly, it would be an advantage in the art to provide an apparatus for remotely coring a body part such as the heart, blood vessels, the stomach, intestines, and other body parts. It would be a further improvement to provide methods of using such an apparatus to core such a body part. It would also be an improvement in the art to provide a device for remotely cannulating a body part, including an apparatus for remotely cannulating a body part such as the heart, blood vessels, stomach, or intestines of a patient. It would be still another improvement in the art to provide methods for using such a device. It would also be an improvement in the art to provide remote cannulation apparatus that allow coring and/or cannulation of a body part while preventing the introduction of embolic materials into the patient and excessive loss of blood.

Such methods and apparatus are disclosed herein.

SUMMARY OF THE INVENTION

The apparatus and methods of the present invention have been developed in response to the present state of the art, and in particular, in response to the problems and needs in the art that have not yet been fully solved by currently available methods and apparatus for remotely coring and cannulating a body part such as a heart, blood vessel, stomach, segment of the intestines, or other body part. Thus, the present invention provides apparatus and methods for remotely coring and remotely cannulating a body part. In the case of procedures involving the heart, the methods of the invention may be used to remotely install heart assist or replacement devices.

Treatments for heart disorders or diseases may call for the installation of ventricular assist devices or heart replacement devices. Previous methods for installing such devices required the creation of a large opening in the chest cavity of the patient to allow access to the heart for installation. Additionally, these methods often call for cardiopulmonary bypass methods to be used in order to reduce the risk of emboli during the coring of the heart and the insertion of the device.

The method and apparatus of the invention allow for remote coring of a body part, such as a heart, to allow remote installation of a cannula and an inlet conduit, which may then be coupled to heart-replacement devices, ventricular assist devices, or other similar apparatus. Specifically, the method of the invention provides a remote or minimally invasive apparatus and method for coring the wall of the heart, attaching an inflow cannula, and removing the core from the body. The method decreases the risk of emboli and may reduce the need for cardiopulmonary bypass. The method may additionally reduce the loss of blood involved in such surgeries, and may improve the comfort of the patient by minimizing the need for thoracotomy (incision into the thorax) or sternotomy (incision into the sternum) by allowing the installation of a heart assist or replacement device without requiring direct surgical access to the heart. This may also reduce the recovery time needed after such a surgical procedure. In some preferred methods, the method includes installing a cannula by coring into the left ventricular apex of a heart.

Further, the invention provides apparatus to effect the cannulation, namely an endoscopic cannulation apparatus. The cannulation apparatus includes a fluid stasis assembly and a coring assembly mounted about an endoscopic shaft. The remote cannulation assembly may first include a trocar tip for penetrating the body part. The trocar may be mounted on an end of the shaft. The trocar allows the cannulation apparatus to pierce the tissue of the heart and be admitted into the interior of the heart. The trocar may be equipped with a port for an endoscope or other pressure-monitoring device to allow detection of when the trocar has pierced the wall of the heart. This allows advancement of the trocar to a proper depth in the heart without causing unintentional damage.

The shaft of the cannulation apparatus of the invention may be a hollow endoscopic shaft, and may be flexible or rigid. The shaft allows for improved remote access to the heart, and potentially for reductions to surgical trauma. The shaft may additionally include a second shaft positioned internally or externally to the first shaft. At least one of these shafts may be rotatable to drive the coring assembly when a rotating cutting device is being used.

The fluid stasis assembly of the invention is mounted about the shaft and configured to travel along the length of the shaft in a guided fashion. The fluid stasis assembly includes an occlusive device mounted about the shaft. The occlusive device has a deployed configuration and a stowed configuration. The shape and size of the occlusive device may be varied within the scope of the invention to include occlusive devices such as devices which provide a seal by being drawn or pressed against the tissue of the body part. The devices may be stowed in a compact configuration for positioning inside or outside of a body part, and then deployed on demand. When deployed, such occlusive devices may be configured to generally adopt a shape and/or size which prevents fluid and gas flow past the device. Suitable occlusive devices include inflatable balloons, umbrella-shaped occlusive devices, disk-shaped occlusive devices, and resorbable occlusive structures.

In use, the occlusive device may be mounted such that it may be advanced and retracted along a length of the shaft. In some embodiments, the occlusive device may be mounted directly to the shaft. In others, the occlusive device may be attached to an intervening slidable mount. This allows for proper initial placement and inflation of the occlusive device within or without a body part such as the heart. It also allows for later placement of pressure or tension on the occlusive device to assure the creation of a seal with the wall of the body part. The occlusive device may additionally comprise at least one de-airing port on the surface that faces the wall of the body part where the core will be removed. Such a port could emit saline solution, blood, plasma, artificial blood substitute, Ringer's solution, or other suitable solution into the system to help remove bubbles and debris.

In addition, the endoscopic cannulation apparatus includes a coring assembly. The coring assembly may be attached about the shaft of the cannulation assembly such that it can be advanced and retracted up and down the shaft. The coring assembly may additionally be attached to the shaft such that it may be driven forward and/or rotated to core the body part. In some embodiments, the coring assembly may be at least partially enclosed by a protective sheath. The sheath may enclose the coring assembly, and in some embodiments may enclose at least a part of the occlusive device in a manner such that the coring assembly is not exposed prior to placement and deployment of the occlusive device.

The coring assembly of the invention may be varied within the scope of the invention. The coring assembly generally includes a cutting tool such as a blade attached about the shaft such that the blade may be advanced and retracted along the shaft. The blade may be a metal blade having at least one sharpened edge. Such a blade may be configured to be compressed from its normal shape and position while contained within the sheath, and then be deployed to its intended configuration by the resiliency of the material from which it is made upon removal of the sheath.

Alternatively, the blade may be a cylindrical elastic cutting tool for coring the body part. The blade may alternatively be a hydrojet cutter used to core the tissue of the body part. Other suitable cutting devices known in the art could be included in the coring assembly of the invention.

In some embodiments of the invention, the coring assembly may further include a core retainer. The core retainer is configured to assist in the withdrawal of the core of tissue cut from the body part by the blade from the body. The structure of such a core retainer may vary with the structure of the coring assembly. In one embodiment of the endoscopic cannulation assembly of the invention, the core retainer is a helical ridge positioned on the coring assembly. This helical ridge is configured to engage the core cut from the body part to allow its withdrawal from the body. In some cases, the helical ridge may be positioned on a coring assembly base to which the blade or blades are mounted that is slidably positioned on the shaft. As such, this particular core retainer holds the core of tissue with a helical ridge positioned inside of the hole in the core produced by the trocar.

In other embodiments of the coring assembly, the core retainer is configured to grasp the core cut from the body part on its outside surface. In one such example, the core retainer comprises a helical ridge positioned on an inside face of an elastic cylindrical coring tool, the helical ridge being configured to engage the outside surface of the core cut from the body part to allow its withdrawal from the body.

The endoscopic cannulation apparatus of the invention may additionally include a guard situated between the occlusive device and the coring assembly to protect the occlusive device from contact with the coring assembly. In some cases, the guard is attached to the occlusive device. This might take the form of a protective layer of a damage-resistant material attached to the occlusive device, segments of such a material attached to regions of the device, or even possibly regions of the occlusive device that are thickened or reinforced.

The endoscopic cannulation assembly of the invention may be used with a cannula attachment ring that is anchored to the body part to be cannulated to provide an anchor for the cannula. The ring attaches to the body part, and the cannula attaches to the attachment ring. This may be accomplished using rings of varying designs, including those having a locking ring associated with the attachment ring. In such attachment rings, the locking ring may expand as the cannula passes through it, locking the cannula into place. Alternatively, the locking ring may interact with surface or design features of the cannula to otherwise engage the cannula and secure it. The attachment ring may alternatively be provided with threads on an inside diameter to which the cannula could later be attached. It may also have external threads (or other attachment means) to which tools used in the coring and cannulation process described herein may be attached.

The invention further includes methods for remotely cannulating a body part using an endoscopic cannulation assembly. The method uses the endoscopic cannulation assembly described above, broadly having an occlusive device, and a coring assembly. The method includes steps such as affixing a cannula attachment ring to the body part, piercing the body part, deploying the occlusive device to provide fluid stasis, coring the body part, cannulating the body part, and de-airing the assembly.

According to a first general method, the body part is first prepared by attaching a cannula attachment ring to it in order to provide an anchor for the cannula once it is attached. Following this, an occlusive device is placed in abutment to a wall of the body part in preparation for coring. The placement may be brought about by simple placement of the device against an outer wall of the body part. Alternatively, it may require piercing the body part through the center region of the cannula attachment ring with a trocar and inserting the occlusive device. Following this, the occlusive device is deployed and held fast to the wall of the body part in order to provide fluid stasis during the subsequent steps of the method. Following this, the coring tool is deployed in position to cut a core out of the body part. A core is then cut out of the body part using the coring tool, and the core is fixed to the core retainer of the coring assembly to allow removal.

A cannula may then be placed in the body part by moving it along the endoscopic cannulation assembly into place through the cannula attachment ring into the orifice left by the core. Following this, the coring tool, core retainer, and core may be withdrawn from the patient's body through the cannula.

The method may further comprise the step of purging all air from the installed cannula and remote cannulation assembly by using a pressurized source of a physiologically appropriate fluid. This step may be conducted once or repeated at various stages of the method. For example, the assembly may be de-aired prior to the step of forming an opening in the body part. The assembly may additionally be de-aired prior to removing the inflatable balloon, prior to the initiation of the pump, or the de-airing may be conducted throughout the coring and cannulation process.

The cannula used in connection with the endoscopic cannulation assembly may be generally cylindrical in shape and configured to be securely attached to an attachment ring previously mounted to the body part. In some embodiments this may include a retaining groove which integrates with a lock on the attachment ring. The cannula may alternatively include external threads to allow it to securely integrate with the attachment ring.

These and other features and advantages of the invention will become more fully apparent from the following description and appended claims. They will also be learned by the practice of the invention as set forth hereinafter.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 7I is a perspective view of the endoscopic cannulation device of FIG. 7F shown during a de-airing step of the method;

FIG. 7J is a perspective view of the endoscopic cannulation device of FIG. 7F shown after partial withdrawal of the endoscopic cannulation apparatus from the heart;

FIG. 9 is a perspective view of the assembly during a de-airing step of the methods of the invention.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 9, is not intended to limit the scope of the invention, as claimed, but is merely representative of presently preferred embodiments of the invention.

Figure 1:
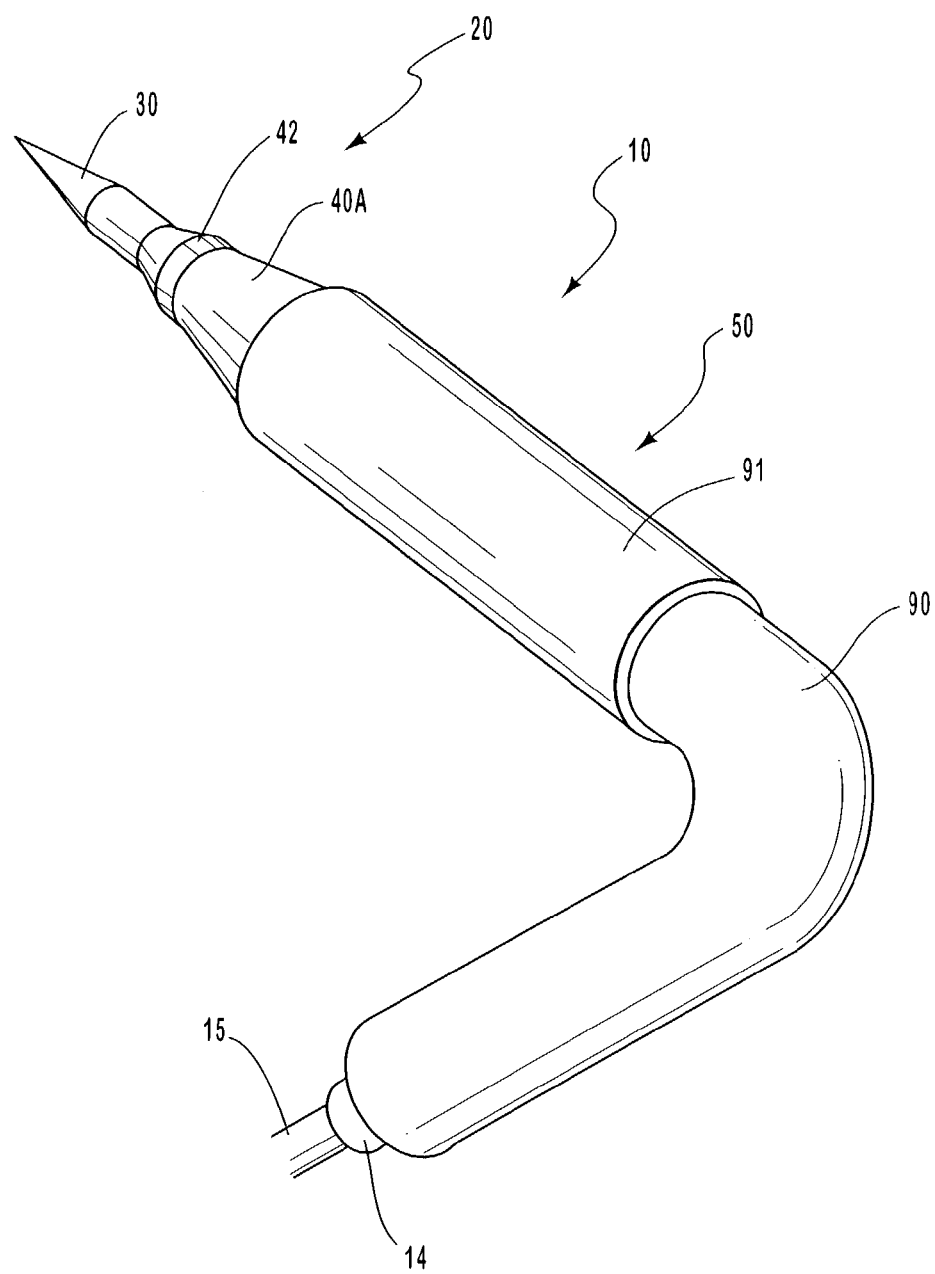
FIG. 1 is a perspective view of an endoscopic cannulation apparatus of the invention.

Referring now to FIG. 1, an endoscopic cannulation device 10 according to the invention is shown isolated in a perspective view. The cannulation device 10 is an endoscopic device configured to provide entry into or an exit from a body part, allow the erection of an occlusive structure to prevent the flow of blood or other fluids out of the body part, cut and remove a core from the body part, and install a cannula into the body part.

The cannulation device 10 includes a fluid stasis assembly 20 shown passing through a cannula 90. The cannulation device 10 further includes a coring assembly which is blocked by the cannula 90. Both of these segments of the invention are attached to a shaft 14 which runs through the cannulation device 10 and out of the patient's body. The shaft 14 may be flexible or rigid. The fluid stasis assembly 20 may include a trocar 30 and an occlusive device 40A. In this example, the occlusive device 40A is an inflatable balloon shown deflated and stowed in a compact configuration. The trocar 30 may be attached to the shaft 14, or may alternatively be attached to an internal shaft 15 passed slidably through the shaft 14. The trocar 30 is an instrument used to pierce the outer tissue of a body part to allow penetration of the fluid stasis assembly 20 of the cannulation device 10 into the body part. The trocar 30 is thus attached to an end of either the shaft 14 or an internal shaft 15. The progress of the trocar 30 through the wall of the body part may be tracked and directed endoscopically.

The inflatable balloon occlusive device 40A of the fluid stasis assembly 20 is configured to slide through the narrow passage created by the trocar 30 into the interior of the body part. The balloon occlusive device 40A may then be inflated and drawn against the inside surface of the segment of the wall of the body part to be cored, thus providing a seal during and after the coring to prevent exit or entry of fluid, gas, or other materials. The balloon occlusive device 40A is slidably mounted about the shaft 14 such that it may be advanced and retracted along the length of the shaft 14. This allows proper deployment and positioning of the balloon 40A. In some embodiments of the invention, this mounting is accomplished by directly attaching the balloon 40A about the shaft 14. In the cannulation assembly of FIG. 1, the balloon 40A is attached to a device mount 42 that is slidable along a length of the assembly 10.

The coring assembly 50 may optionally be housed within a sheath (not shown), and is slidably mounted about the shaft 14. The shaft 14 may be hollow to function as an endoscope, to permit passage of an internal shaft 15, to channel single or multiple flows of fluid, or to admit another endoscope or endoscopic device. In some specific embodiments, an internal shaft 15 passes through the shaft 14, bearing portions of the apparatus 10 such as the trocar 30. Either or both of the shafts 14, 15 may be configured to transmit at least one flow of a fluid, such as saline solution, into or away from the body part being cored and cannulated. In some embodiments, one or more of the shafts 14, 15 can receive or emit a fluid at a point along its length intended to be placed inside the body part to be cannulated. This may aid in the de-airing steps of the invention. The shaft 14 is sized and adapted to travel through a cannula 90 having a myocardial interface 91. The cannula 90 terminates in a screw ring (not shown) that is capable of providing a seal when attached to an inflow conduit of a heart-assist or heart-replacement device (not shown). The shaft 14, cannula 90, and inflow conduit (not shown) may be configured to be flexible to increase ease of use.

Figure 2A:
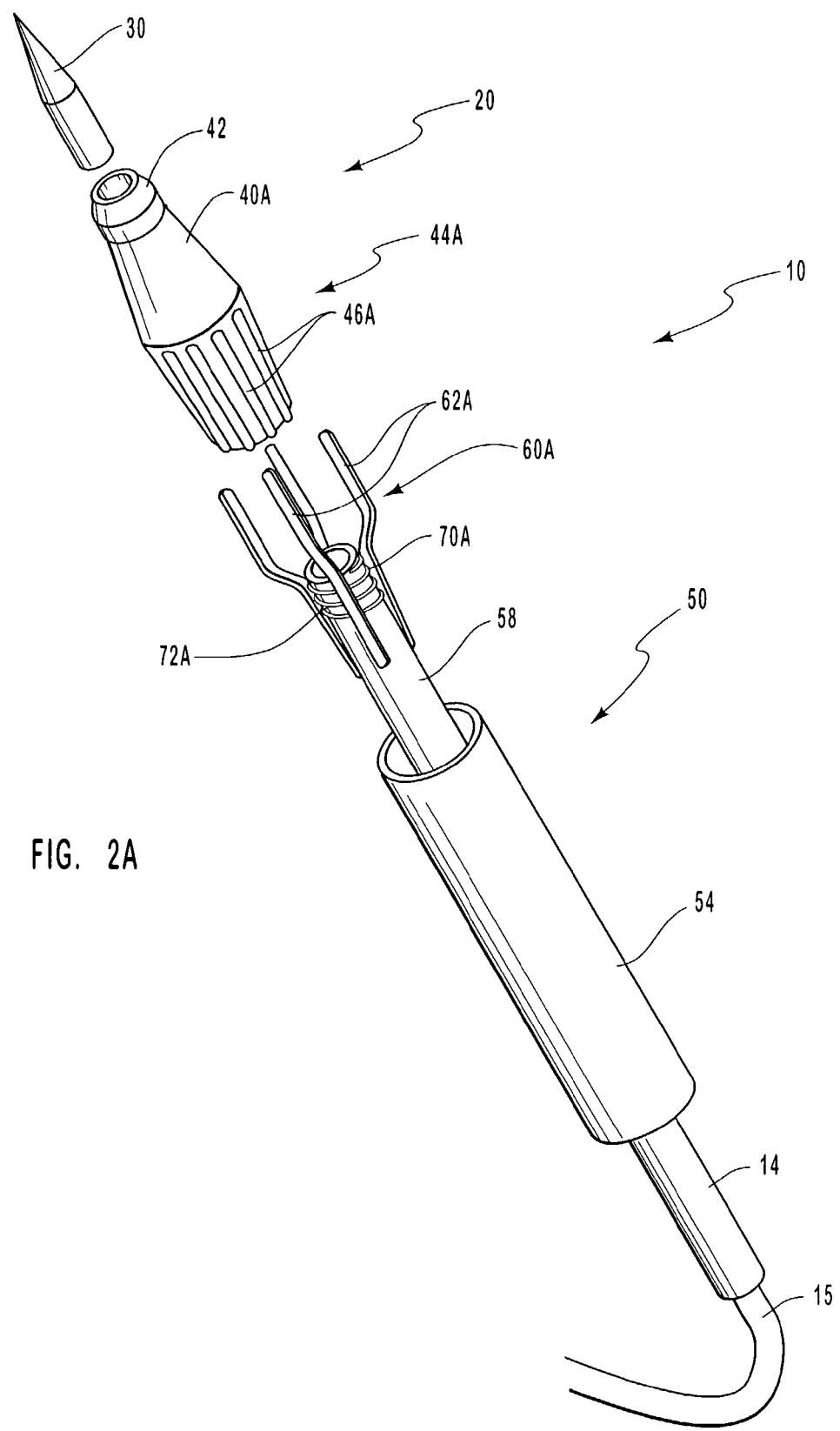
FIG. 2A is an exploded perspective view of the endoscopic cannulation apparatus of FIG. 1.

FIG. 2A is an exploded view of the endoscopic cannulation apparatus 10 of FIG. 1 with the cannula omitted to permit view of the coring assembly 50. As above, the fluid stasis assembly 20 has a trocar 30 at its tip, shown to be attached to a first end of the shaft 15. Following the trocar 30 is the inflatable balloon occlusive device 40A. In use, this component is slidably mounted about the shaft 14. The balloon 40A may be directly mounted to the shaft 14, or it may be attached to a device mount 42 that is slidable along the shaft 14.

As is visible in FIG. 2A, the inflatable balloon occlusive device 40A may further include a guard 44A configured to protect the balloon 40A from the coring assembly 50. In the embodiment of FIG. 2, the guard 44A is made up of a plurality of ridges 46A attached to the inflatable balloon 40A. These ridges 46A are made of a material resistant to damage from the components of the coring assembly 50. In some embodiments of the invention, the ridges 46A may be constructed of a metal, plastic, composite, or other suitable material in solid or mesh form bonded to the balloon occlusive device 40A. The ridges 46A may alternatively be thickened regions of the balloon capable of resisting damage from the coring assembly 50. In still other alternatives, the guard 44A may be a component of the hemostasis assembly placed at the end of the assembly 20 after the balloon 40A. This separate guard component 44A would be configured to deploy between the balloon occlusive device 40A and the coring assembly 50. In such an embodiment, the guard 44A would deploy upon inflation of the balloon 40A or when otherwise triggered. As such, the guard 44A could be conical in shape and attached to the shaft 14.

FIG. 2A further shows the components and relationship of the components of an embodiment of the coring assembly 50 of the endoscopic cannulation apparatus 10 of the invention. Here, the coring assembly 50 is shown to include a blade 60A mounted to a coring assembly base 58, all housed within the optional sheath 54 discussed above. The blade 60A in this configuration is a set of four resilient blades 62A. These resilient blades 62A are stored in a compact configuration in the sheath 54. When the sheath 54 is withdrawn, the resilient blades 62A spring into their final coring position for use.

Figure 2B:
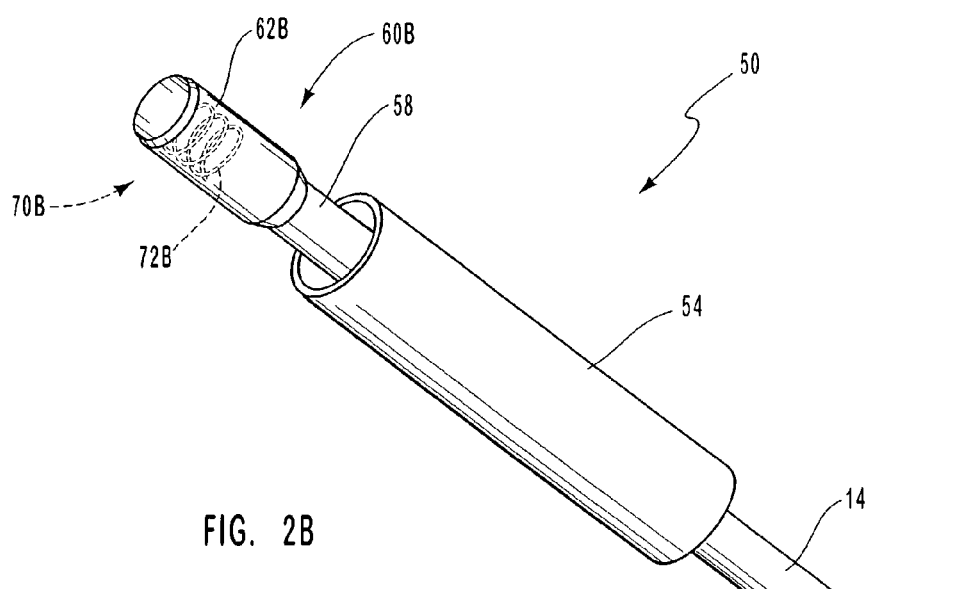
FIG. 2B is an exploded perspective view of the coring assembly of the endoscopic cannulation apparatus of FIG. 2A with a cylindrical coring blade.

The blade 60A may be selected from a wide range of blades configured to core a body part. A first alternative embodiment is shown in FIG. 2B. FIG. 2B shows a view of the coring assembly 50 of FIG. 2A in which the blade 60A (shown in FIG. 2A to comprise flexible blades 62A) comprises a cylindrical cutter 60B. The cylindrical coring device 60B includes a cylindrical coring blade 62B. The cylindrical coring blade 62B may be made of a rigid material, or may alternatively be constructed of a semi-rigid or flexible. The cylindrical coring blade 62B is generally configured to fit within the sheath 54 prior to use in the actual coring step of the method of the invention.

Figure 2C:
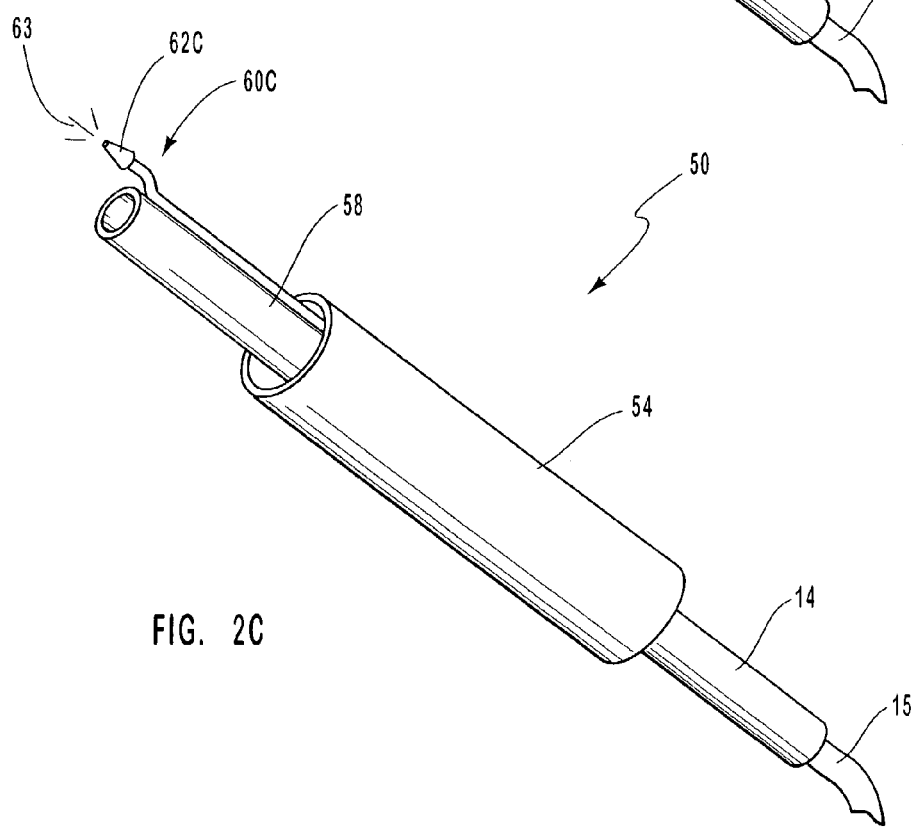
FIG. 2C is an exploded perspective view of the coring assembly of the endoscopic cannulation apparatus of FIG. 2A with a hydrojet cutter device.

A next alternative embodiment of the blade 60C of the coring assembly 50 is shown in FIG. 2C, in which an isolated coring assembly 50 is shown. In FIG. 2C, the coring assembly 50 includes a hydrojet cutter 60C for coring the body part. The hydrojet cutter 60C generally includes a saline jet 62C which emits a jet 63 of a physiologically acceptable fluid such as saline solution. Other physiologically-acceptable fluids such as, but not limited to, saline, blood, plasma, artificial blood substitutes, Ringer's solution, or other compounds known in the art may be used with the hydrojet cutter 60C.

Figure 2D:
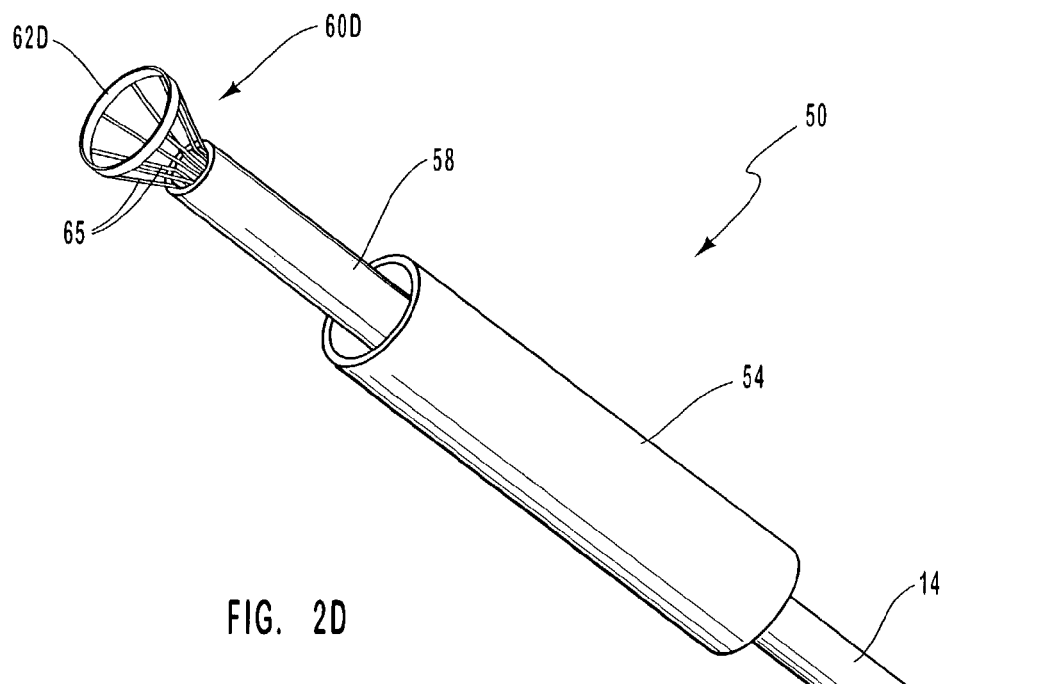
FIG. 2D is an exploded perspective view of the coring assembly of the endoscopic cannulation apparatus of FIG. 2A with a collapsible cylindrical cutter.
Figure 2E:
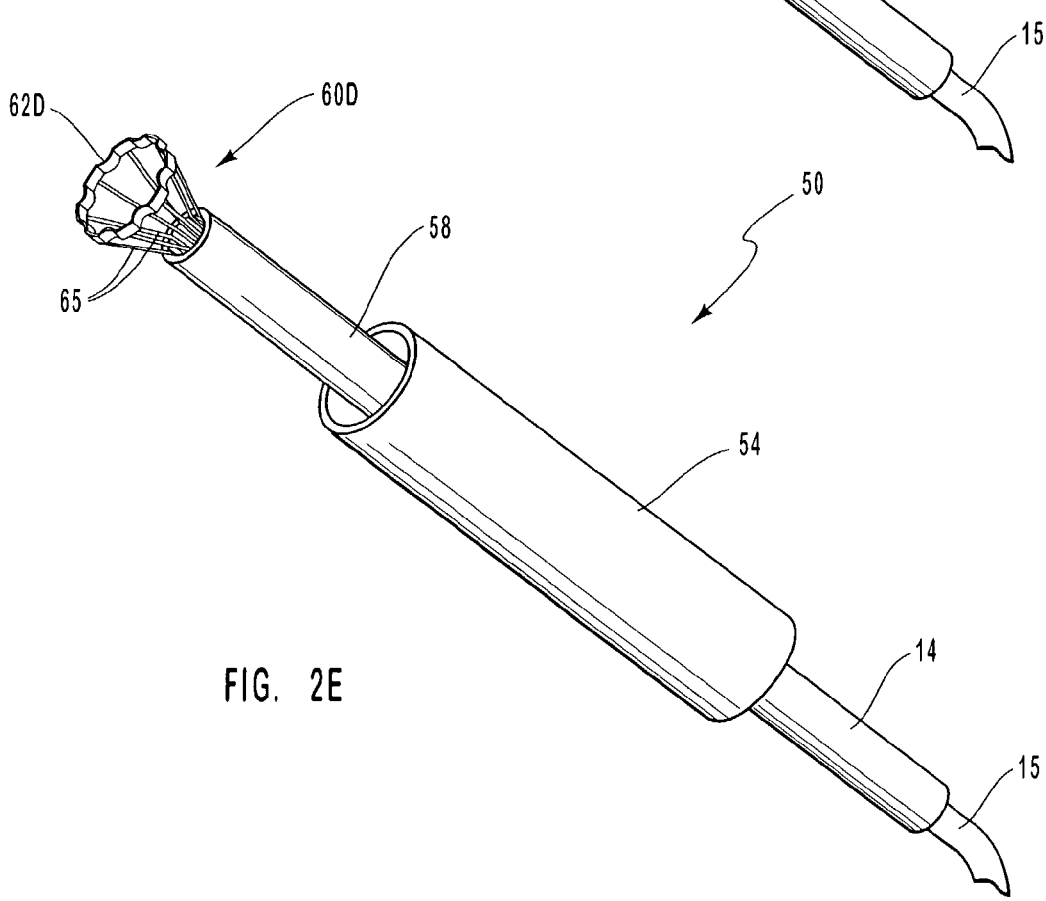
FIG. 2E is an exploded perspective view of the coring assembly of the endoscopic cannulation apparatus of FIG. 2D showing the collapsible cylindrical cutter partially collapsed.

FIGS. 2D and 2E show yet another embodiment of the coring assembly 50 of the invention. In these figures, the coring assembly 50 includes a collapsible cylindrical cutter 60D. In this embodiment, the collapsible cylindrical cutter 60D includes a collapsible cylindrical blade 62D and supports 65. FIG. 2D shows the cylindrical blade 62D in its fully expanded configuration. FIG. 2E shows the cylindrical blade 62D partially collapsed. This configuration may be observed as the cylindrical cutter 60D is being deployed from or retracted into the blade sheath 54. Such cylindrical cutters 60D may be configured to deploy a blade 62D to cut a core that is larger in size than the sheath 54 while remaining capable of being stored within the sheath 54.

The blades 60A-60D of the invention may include flexible and/or rigid components. Additionally, the blades 60A-60D may have cutting surfaces which are one-sided or two-sided. In addition, in embodiments of the blade such as 60A of FIG. 2A having tips, the blade 60A may have a variety of tip characteristics, including sharp and/or pointed-tips. In some configurations, the blades 60A-60D will be mounted to a coring assembly base 58 attached to the shaft 14, the coring assembly base 58 being configured to move slidably along the shaft 14. In some configurations, the blades 60A-60D will be configured to be mounted directly to the shaft 14.

Referring again to FIG. 2A, the coring assembly 50 of the invention may further include a core retainer 70A. In FIG. 2A, the core retainer 70A comprises a helical ridge 72A mounted to the coring assembly base 58. In this configuration, the ridge 72A engages the inside surface of the bore created in the wall of the body part by the trocar 30 when it penetrated the body part. In this embodiment, the ridge 72A engages the inside face of the bore as the blade 60A is driven through the wall of the body part. This engagement allows the core produced to be withdrawn from the body part along with the coring assembly 50.

In embodiments of the coring assembly 50 such as that shown in FIG. 2B, in which the blade 60B is cylindrical in shape, the core retainer 70B may alternatively comprise a feature such as a helical ridge 72B positioned along an inside surface of the blade 60B. In such configurations, the core retainer contacts the outside surface of the core cut by the coring assembly to allow withdrawal of the core from the body.

Figure 2F:
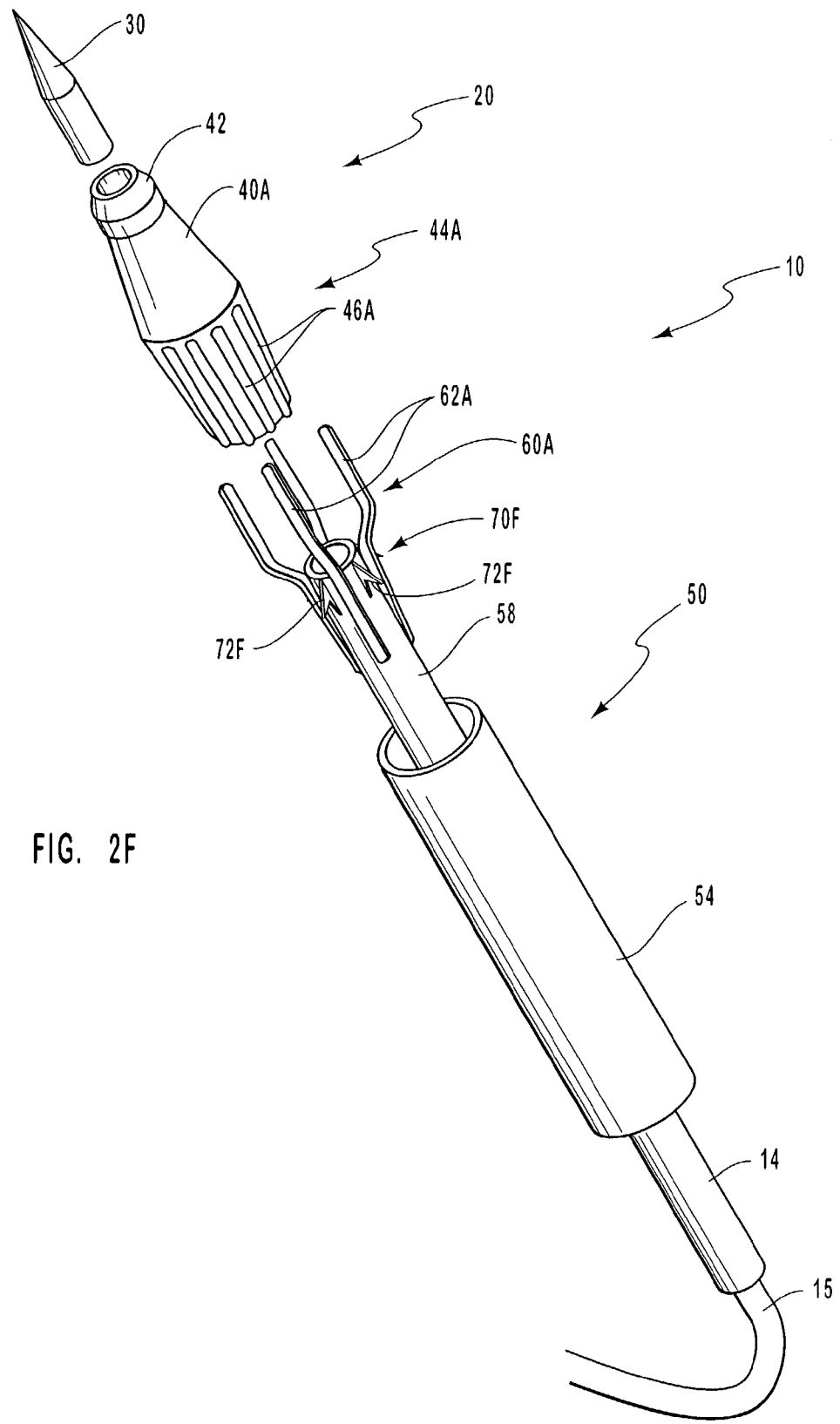
FIG. 2F is an exploded perspective view of the endoscopic cannulation apparatus of FIG. 1 shown with a barbed embodiment of the core retainer.
Figure 2G:
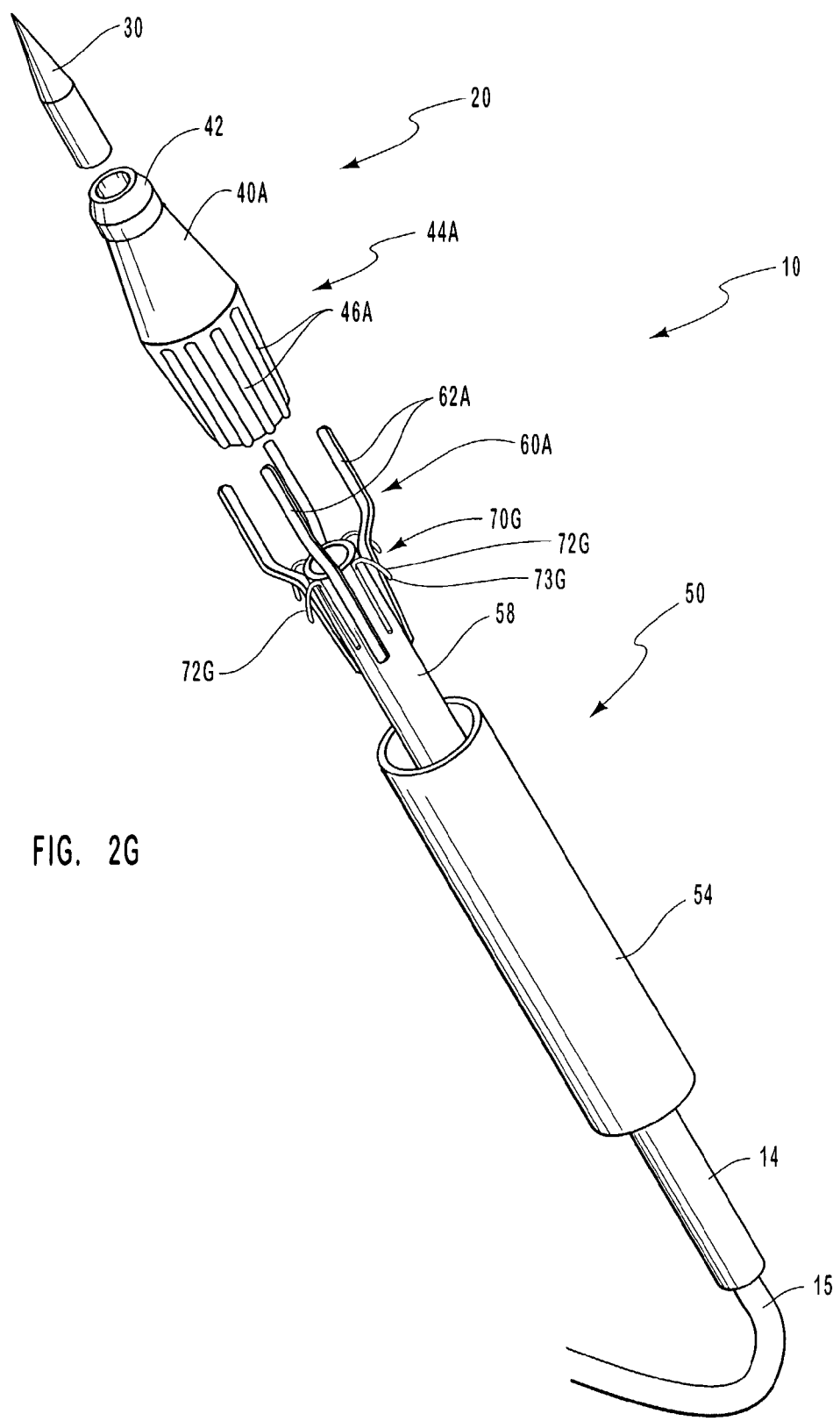
FIG. 2G is an exploded perspective view of the endoscopic cannulation apparatus of FIG. 1 shown with an embodiment of the core retainer including hooks.
Figure 2H:
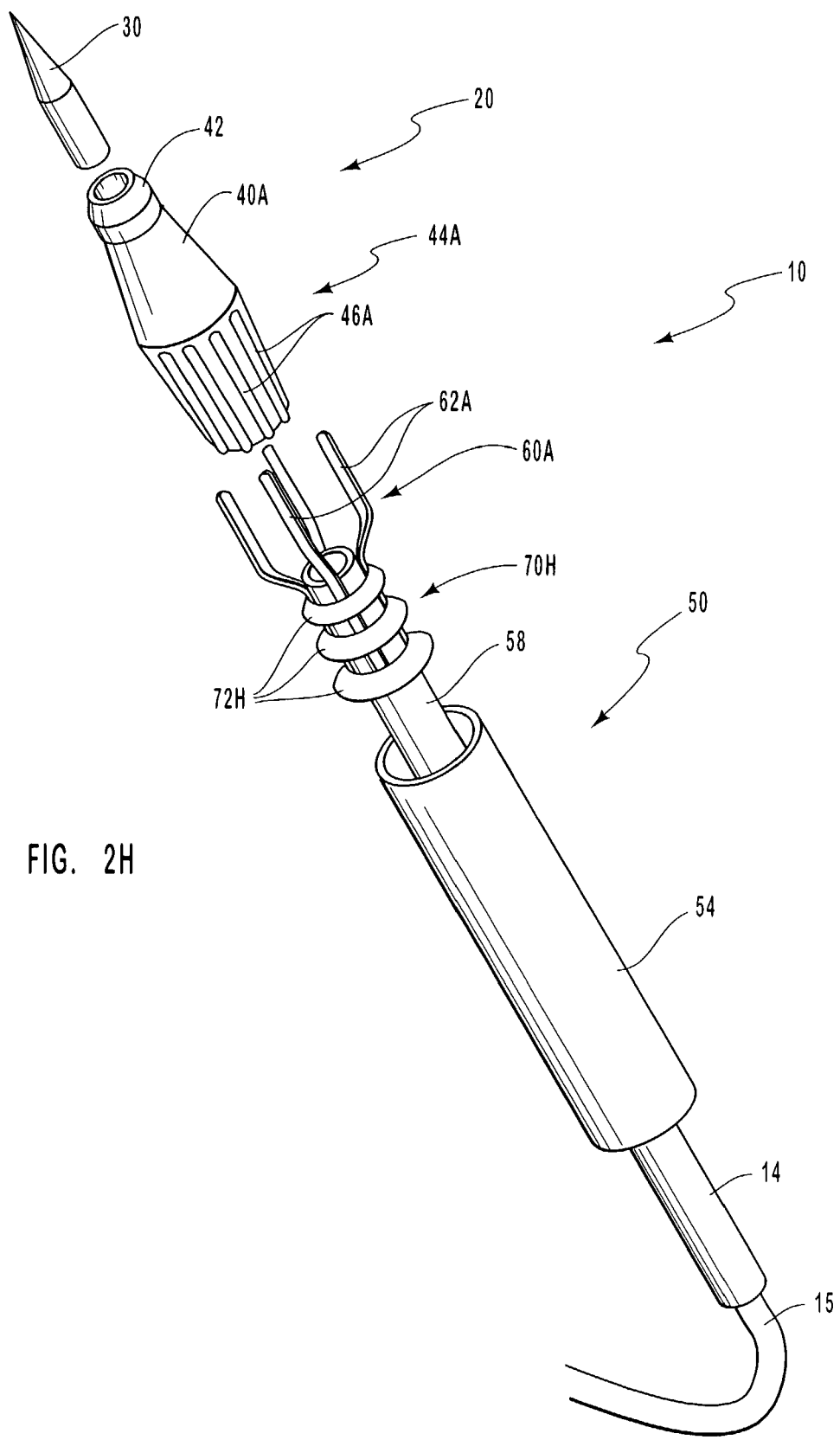
FIG. 2H is an exploded perspective view of the endoscopic cannulation apparatus of FIG. 1 shown with an embodiment of the core retainer including flanges.

The core retainer 70 may take many other forms, including those shown in FIGS. 2F-2H. Referring first to FIG. 2F, the remote cannulation assembly 10 of FIG. 1 is shown with an alternate embodiment of the core retainer 70F. In this embodiment, the core retainer 70F includes at least one barb 72F to engage a core cut from the body part. The barb 72F may have a wide variety of shapes, including that shown in FIG. 2F. In a next embodiment, shown in FIG. 2G, the remote cannulation assembly 10 includes a core retainer 70G having at least one hook 72G to engage the core cut from the body part. In the core retainer 70G of FIG. 7G, the hooks 72G are shown mounted to the coring assembly base 58. The hook 72G is configured to engage the core cut from the body part and retain it. In some embodiments of the invention, the hook 72G may have tips 73G which may either be blunt or sharpened.

FIG. 2H shows still another remote cannulation device 10 having an alternate embodiment of the core retainer 70H mounted about the coring assembly base 58. In this embodiment, the core retainer 70H includes at least one flange 72H attached about the base 58. Here, the core retainer 70H is shown having three flanges 72H which may be composed of a flexible or rigid material for gripping a core cut from a body part.

The invention further includes methods for remotely coring and cannulating a body part using the endoscopic cannulation assembly 10 of the invention such as that described above. Steps of the method will be illustrated in FIGS. 3-6 using the cannulation assembly 10 of FIGS. 1-2A as an example. Each of the steps of the method is discussed in detail below. The discussion will be directed to the coring and cannulation of a heart through the apex of the left ventricle. It should be understood, however, that the steps of the method may be varied within the scope of the invention to core and cannulate other regions of the heart, such as the atria, as well as other body parts including blood vessels, the stomach, and the intestines.

The exemplary method for coring and cannulating a heart discussed hereafter may be used in procedures used to attach a cannula to link the heart to a pump such as a ventricular assist device, and are accomplished while sealing off the interior of the heart from the region to be cored. This prevents the introduction of air bubbles, fluids, and solid embolic particulates into the circulatory system of the patient.

Figure 3:
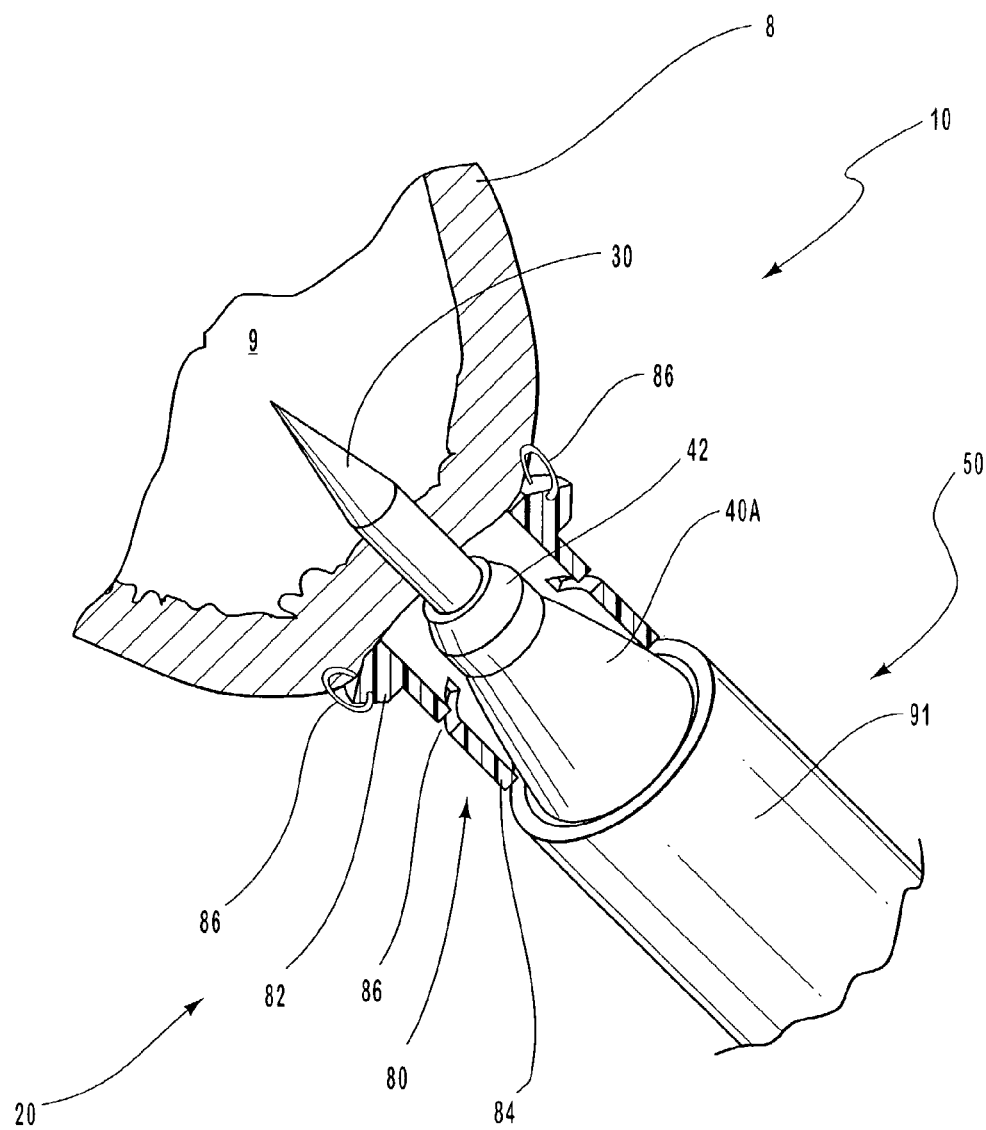
FIG. 3 is a perspective view of the endoscopic cannulation apparatus of FIG. 1 shown partially inserted into a heart.

FIG. 3 shows the results of the initial steps of the method to provide access to the interior of a heart 8. First, a cannula attachment ring 80, (or "apical ring") having an attachment ring 82 and a locking stem 84 is mounted on the left ventricle 9 of the heart 8 to provide an anchor for the cannula (not shown). Typically, the ring 82 is mounted around the point where it is intended to insert the endoscopic cannulation tool 10. The apical ring 80 may have a variety of features to support different methods of attaching the cannula to the apical ring 80. Such features may include screw threads and other surface features placed on the cannula to interface with the apical ring 80.

As shown in FIG. 3, the apical ring 80 may additionally include an attachment ring 82 of physiologically-acceptable felt by which the ring 80 may be attached to the body part. One currently preferred method for this attachment is to suture the apical ring 80 to the apex 6 of the heart 8. This may be conducted using long-handled, remote suturing devices such as would be used in minimally invasive surgery. Surgical staples or other means could alternatively be used. The apical ring 80 may also include a locking stem 84. The locking stem 84 may include slots 86 for engaging a locking ring or surface features on the cannula such as screw threads. One of skill in the art would understand that the features of the apical ring 80 may be adapted to accommodate different attachment methods known in the art, and for use with a variety of body parts.

As is further shown in FIG. 3, following the attachment of the apical ring to the heart, the endoscopic cannulation device 10 is positioned at the intended insertion point on the heart 8. This point is generally located in the center of the previously-placed apical ring 80. It should be understood that for the purposes of a Right Ventricular Assist Device ("RVAD"), Bi-Ventricular Assist Device ("Bi-VAD"), or Total Artificial Heart ("TAH") the invention could be used in a similar means to affect blood path access either to the heart or vascular system of a patient.

Having properly positioned the device 10, the tip of the trocar 30 is then inserted to an appropriate depth into the heart 8, as seen in FIG. 3. The depth of the trocar 30 may be determined fluoroscopically, via ultrasound, via indication ports or transducers on the trocar 30 that allow for indication of ventricular pressure, or using other methods known to those of skill in the art. The trocar tip 30 is stopped after sufficient penetration into the heart 8, thus allowing for insertion of the balloon occlusive device 40A to the appropriate depth as determined using similar methods.

Figure 4:
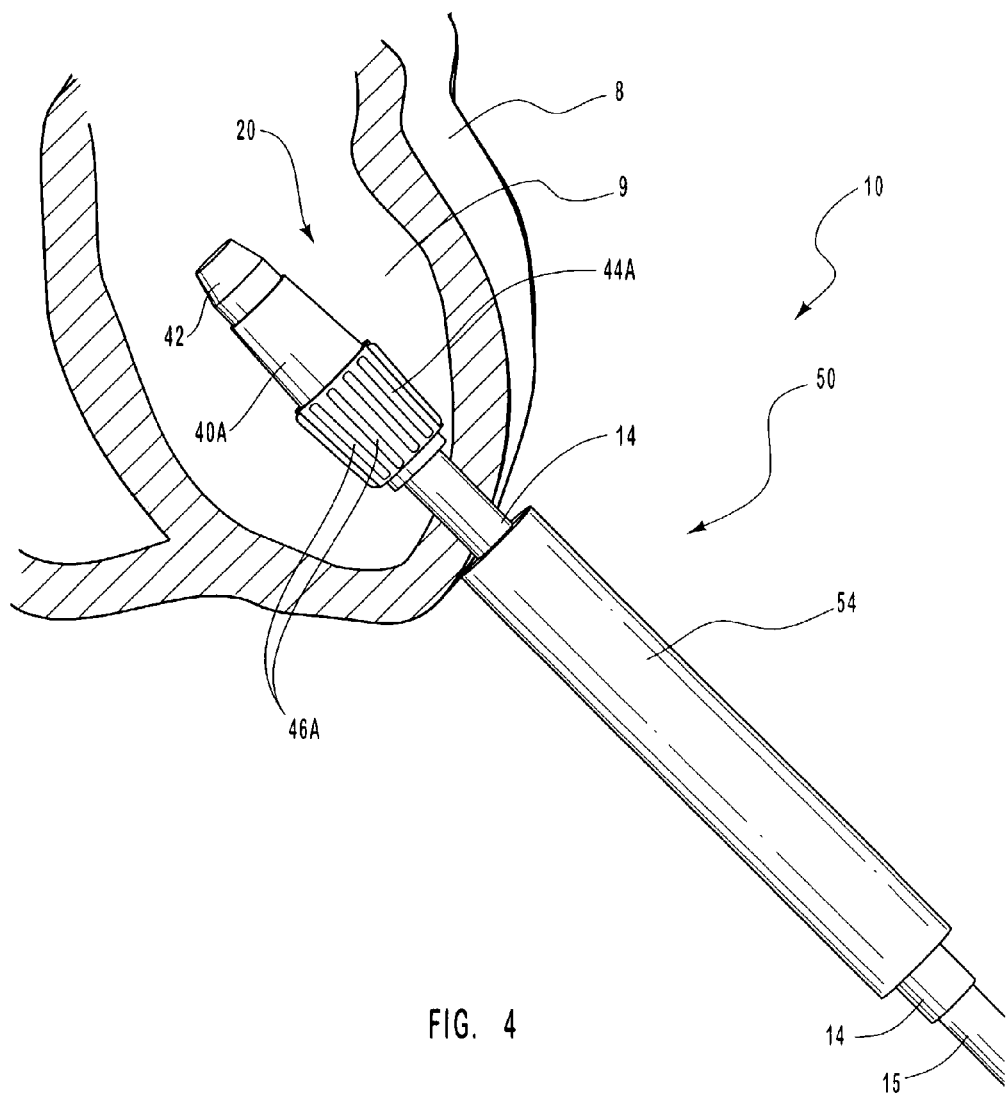
FIG. 4 is a perspective view of an endoscopic cannulation apparatus shown inserted into a heart (shown in cross section) showing the trocar retracted, the sheath partially retracted, and the occlusive device ready for deployment.

FIG. 4 shows a perspective view of the remote cannulation apparatus 10 with the hemostasis assembly 20 placed within the heart 8. The cannula previously shown has been omitted to permit view of the coring assembly 50. In FIG. 4, the placement of the hemostasis assembly 20 in the heart 8 is visible. Specifically, the occlusive device mount 42, the occlusive device 40A, and the guard 44A are shown in position for use. The coring assembly 50 is visible outside of the heart 8 within sheath 54 used to secure the blade of the coring assembly 50 prior to deployment. The coring assembly 50 is as yet retained within its sheath 54 prior to deployment. After deployment, the coring assembly 50 may be rotated using a rotatable shaft 14 positioned rotatably and slidably over an internal shaft 15. The shaft 14 may be driven using means known to one of ordinary skill in the art.

Figure 5A:
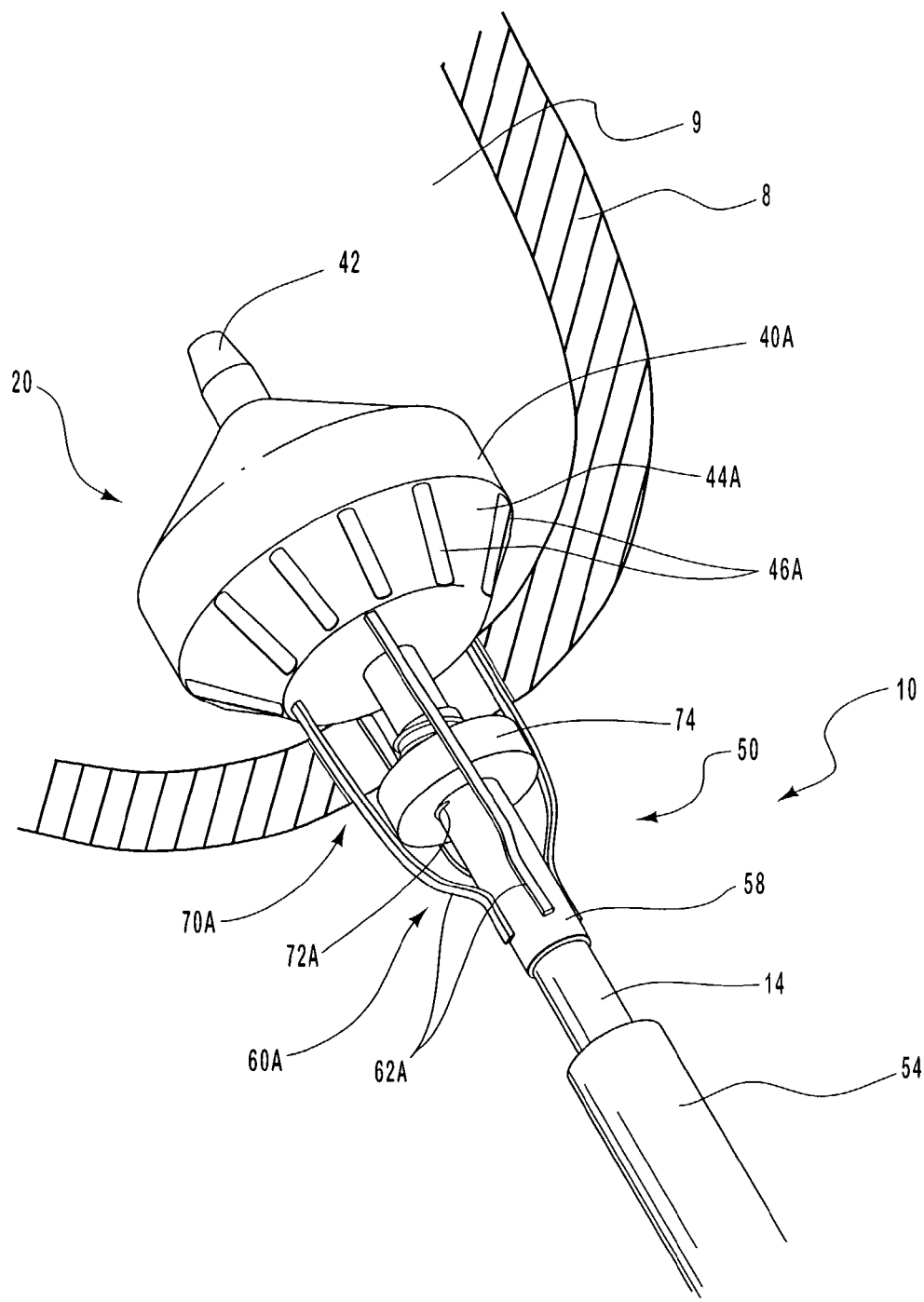
FIG. 5A is a perspective view of the endoscopic cannulation device of the invention with the occlusive device and the blades deployed, the device shown having cut a core from the wall of the heart (shown in cross section)

As illustrated in FIG. 5A, in a next step of the method, the balloon 40A is inflated for use as an occlusive device to create a seal with the ventricular wall of the heart 8. This prevents fluid and/or air flow around the device 10. To provide proper fluid stasis, the connections of the various components of the device with the shaft 14 and the shaft 15 must be made to be sealed to prevent leakage of blood from the heart 8 or of the physiologically-acceptable fluid from the system 10. Other occlusive devices that expand, inflate, or otherwise seal the entry bore into the heart 8 may be used to provide the needed occlusion.

Figure 5B:
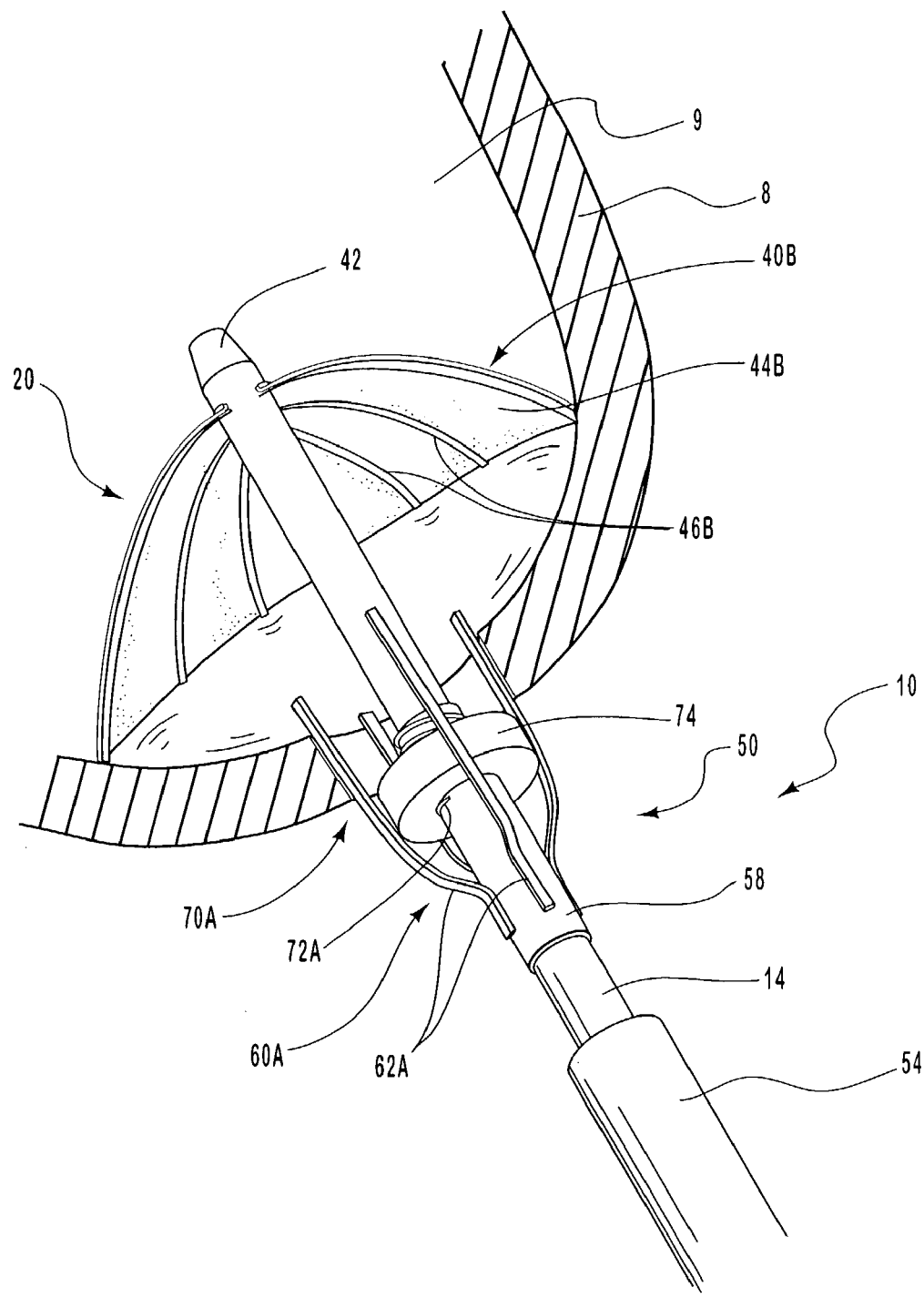
FIG. 5B is a perspective view of the endoscopic cannulation device of the invention with an umbrella-shaped embodiment of the occlusive device deployed, the device shown having cut a core from the wall of the heart (shown in cross section)
Figure 5C:
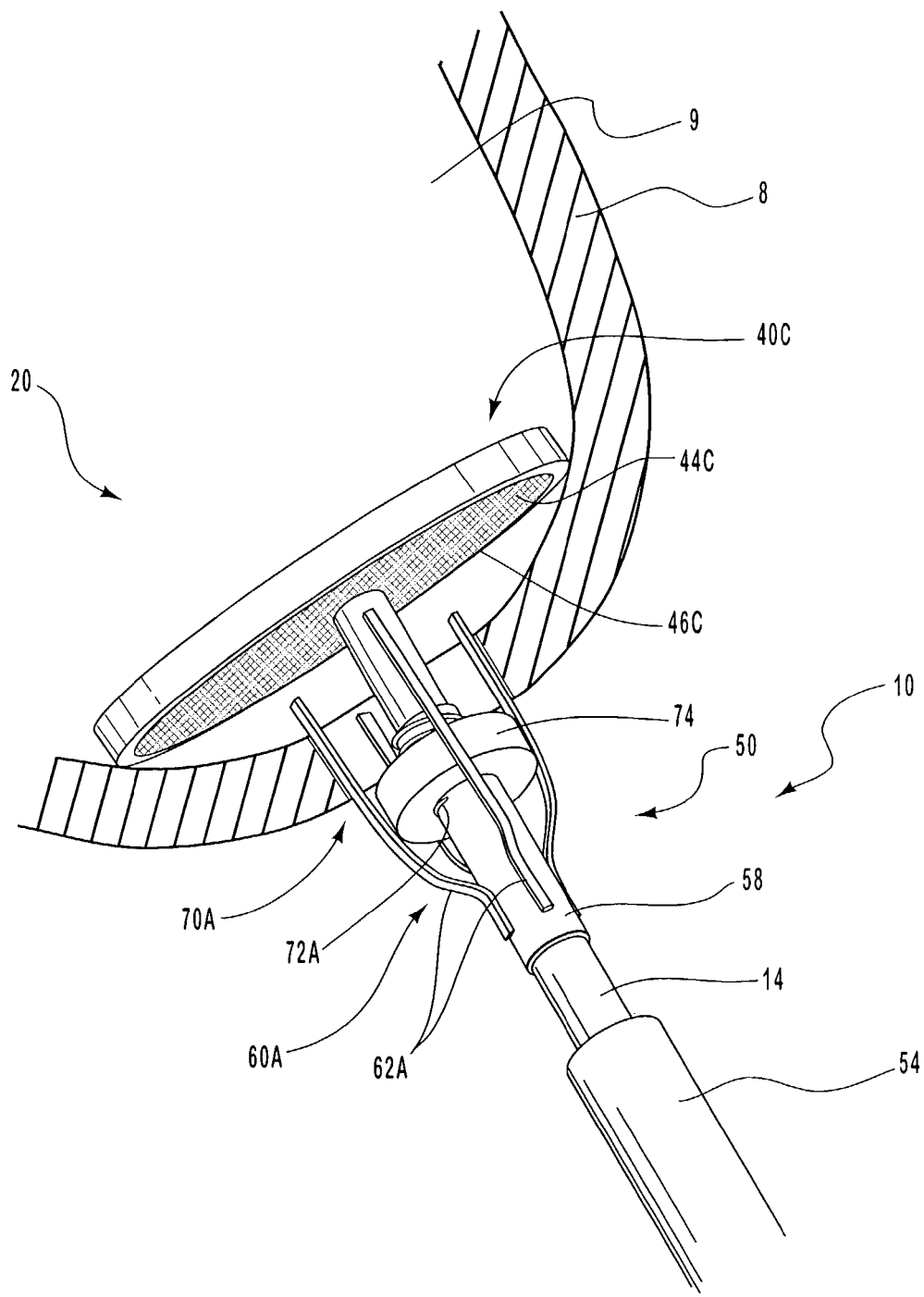
FIG. 5C is a perspective view of the endoscopic cannulation device of the invention with an occlusive disk embodiment of the occlusive device deployed, the device shown having cut a core from the wall of the heart (shown in cross section)

One such alternate occlusive device 40B is shown in FIG. 5B. Specifically, FIG. 5B shows an occlusive device 40B having an umbrella-like shape shown in cross-section. The umbrella-shaped occlusive device 40B may be stored similarly to the balloon occlusive device 40A of FIG. 5A, and then deployed much as an umbrella is deployed and then drawn against the interior surface of the heart 8 to form a seal and to permit coring of the heart 8. Yet another alternate occlusive device 40C is shown in FIG. 5C. More specifically, FIG. 5C shows an occlusive disk 40C deployed in the heart 8 to provide a seal and prevent leakage of fluid into or out of the heart 8. The disk 40C may be inflatable, or may be collapsible like the umbrella-shaped occlusive device of FIG. 5B. As with the other occlusive device embodiments, the occlusive disk device 40C may be stored in a more compact configuration prior to deployment.

Figure 5D:
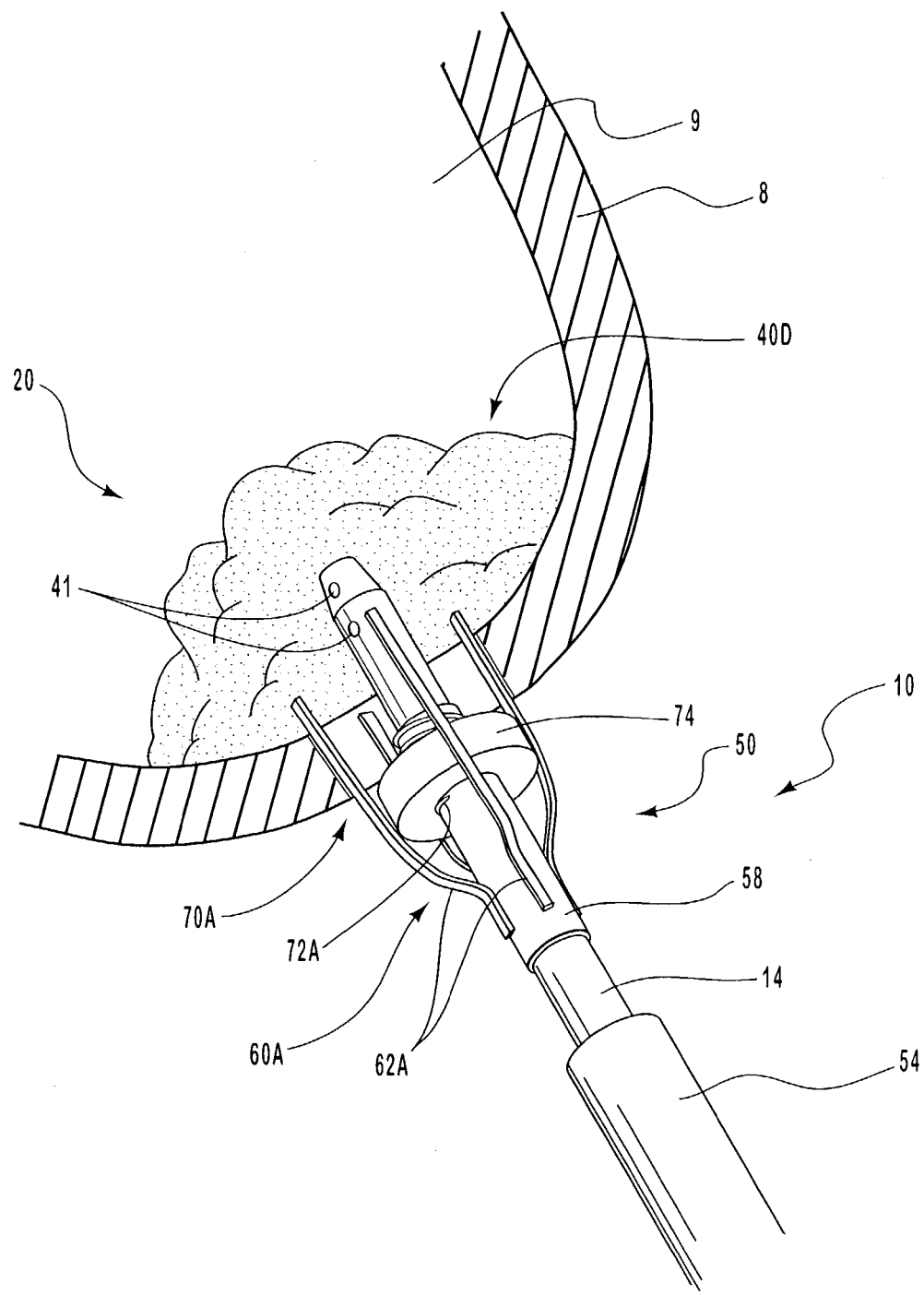
FIG. 5D is a perspective view of the endoscopic cannulation device of the invention with an occlusive gel embodiment of the occlusive device deployed, the device shown having cut a core from the wall of the heart (shown in cross section)

Another alternative occlusive device 40D is shown in FIG. 5D. The occlusive device 40D of FIG. 5D is a barrier composed of a fluid injected into the heart 8 through orifices 41 in the shaft 14. In this embodiment, the occlusive device 40D may be formed by emitting a fluid that can form a gel occlusive structure 40D. The gel occlusive structure 40D would then be resorbed later by the blood. Alternatively, the gel occlusive structure could be partially withdrawn from the heart by drawing it through the orifices 41 back into the shaft 14. Any remaining portions of the occlusive structure 40D would then be resorbed by the blood. Fluids used to form the structure 40D could include compounds such as gelatin, polyethylene glycol ("PEG"), hyaluronic acid ("HA"), collagen, polylactic acid ("PLA") and various mixtures of similar resorbable materials.

Referring again to FIG. 5A, inflation of the balloon occlusive device 40A may also deploy the guard 44A between the hemostasis assembly 20 and the coring assembly 50. In some alternative embodiments, guards 44A might be either unnecessary or might take alternative forms. Such alternative forms of the guards indicate that the coring assembly 50 has progressed fully through the muscular walls of the ventricle 9, and protect the balloon 40A or other occlusive device from damage. FIG. 5B shows a cross-sectional view of a suitable guard 44B. In FIG. 5B, the guard 44B is made up of integrally reinforced regions 46B of the occlusive device 40B. In some embodiments, this is a mere thickening of the material of the occlusive device 40B. In others, however, the integrally reinforced regions 46B include layers, strips, or particles of a damage-resistant material bonded to the occlusive device 40B.

Finally, referring now to FIG. 5C, in an alternate embodiment of the invention, the guard 44C may be a separate component placed between the occlusive device 40C and the coring assembly 50. In FIG. 5C, the guard 44C is a separate component deployed with the occlusive device 40C that resists damage from the coring assembly 50 and serves to indicate complete passage of the coring assembly 50 through the wall of the heart 8. In this embodiment, the guard 44C is a disk-shaped member composed of a damage-resistant mesh 46C. In alternate forms, this guard 44C could be composed of other materials.

As illustrated in FIGS. 5A through 5D, following proper placement of the fluid stasis assembly 20, the heart 8 may be cored, and the core may be removed. The coring assembly 50 is first deployed by retracting the sheath 54. Deployment of the coring assembly 50 exposes the blade 60A for use. In this embodiment, the blade 60A includes resilient blades 62A and a coring assembly base 58 connected to a rotatable shaft 14. The blades 62A are resilient metallic devices that are previously collapsed inside the sheath 54 and deploy by expanding when the sheath 54 is displaced. The blades 62A may be sharp on one or both edges, and may have a variety of tip characteristics. The specific tip characteristics may be selected with reference to the guards 44A-44C. In some embodiments, it is desirable that the contact of the blades 62A with the guards 44A-44C indicates complete penetration of the body part without damaging the occlusive device 40A-40D. The coring assembly base 58 serves as a mount for the blades 62A, and is also attached to the rotatable shaft 14. The rotatable shaft 14 may be flexible or rigid, and is slidably and rotatably mounted about the shaft 15 of the apparatus 10. In alternative embodiments of the invention, the blades 62A may be mounted directly to the rotatable shaft 14 without use of a base 58.

In alternate embodiments of the invention, the blade 60A could be an elastic cylindrical cutting tool, a hydrojet cutter, or any other appropriate dissection tool as seen as FIGS.

2A-2E. Further, because hemostasis is provided, the blade 60A could also be a separate device such as a manually-wielded cylindrical cutting tool. These devices either include, or are generally capable of being associated or aligned with a centrally located sleeve or attachment to access at least one of the shafts 14, 15 of the device in order to align the blade 60 with the cutting guard 44.

As shown in FIG. 5A, the coring assembly 50 includes a core retainer 70A including a raised ridge 72A, shown having a helical pattern, on the coring assembly 50 that provides for retention of the cored myocardial tissue 74. The core retainer may have a variety of configurations, including ridges of other geometries, as well as barbs, hooks, or flanges protruding from the base 58, blade 60A, or shaft 14 that could provide similar retention of the core. The retainer could further be incorporated into the blades 62A. Several such embodiments are shown in FIGS. 2F-2H.

Having deployed the blade 60A, the coring assembly 50 is then rotated using the rotatable shaft 14, thus advancing it through the myocardium of the heart 8. This creates a cylindrical hole, while capturing the cored tissue 74 on the core retainer 70A. The advancement is continued until the blades 62A contact the guard 44A and complete cutting the core 74. Following this, the rotation may cease, and the core 74 and blade 60A may be withdrawn into the sheath 54 and removed from the body.

In FIG. 5, the core 74 is shown being removed while the balloon occlusive device 40A remains in place to provide hemostasis. The device may be configured such that the core 74 can readily be compressed to a dimension that allows its withdrawal with the endoscopic cannulation apparatus 10 through the successfully-installed inflow cannula (not shown).

Figure 6:
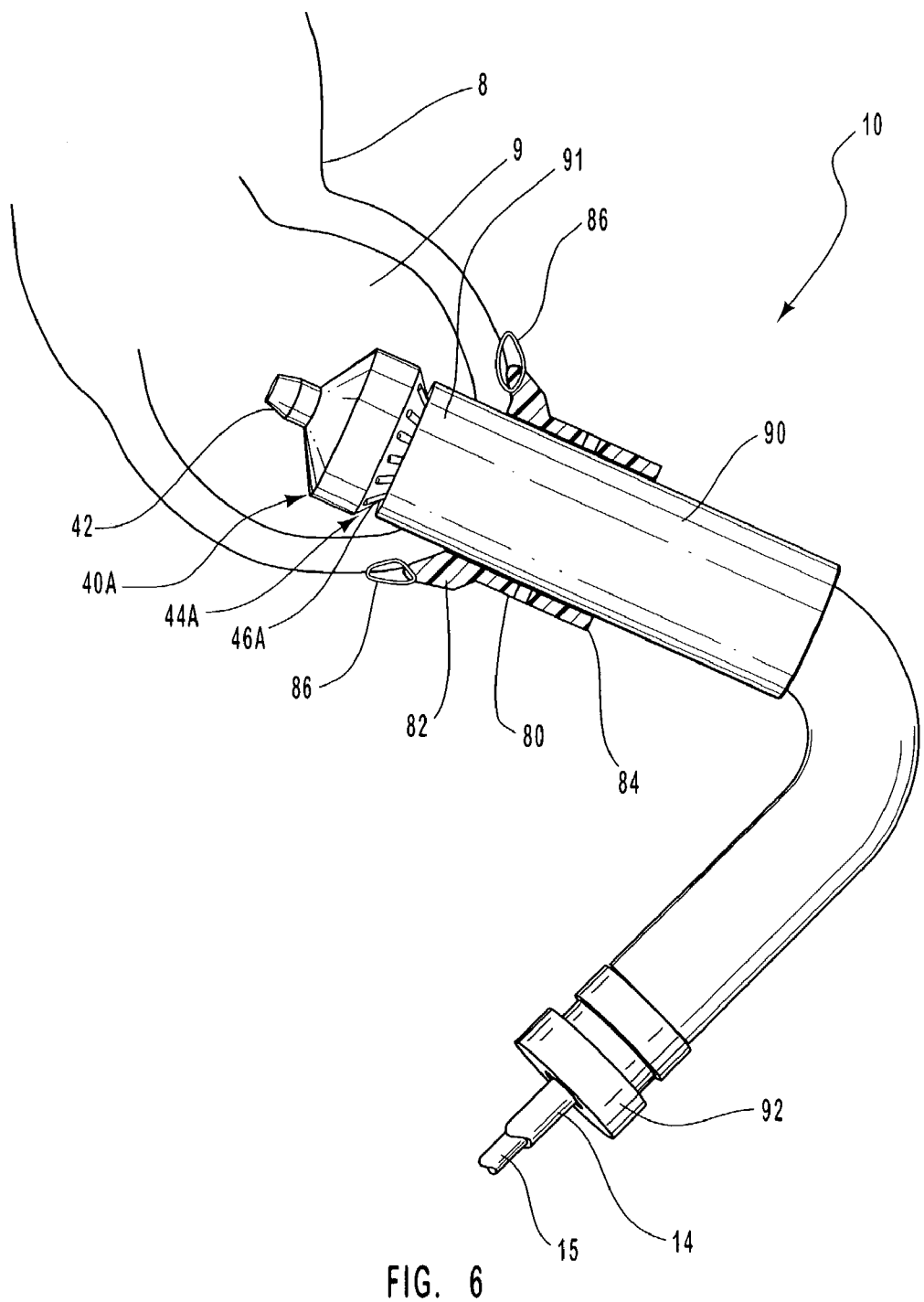
FIG. 6 is a perspective view of the endoscopic cannulation device of the invention shown after insertion of a cannula into a heart (shown in cross section)

Referring now to FIG. 6, following proper coring of the heart 8, the cannula 90 is positioned about the shaft 14 of the device 10, and the cannula 90 is advanced to a point at which it interacts with the ventricular wall, and may further be advanced into the ventricle 9 of the heart 8. In this embodiment of the invention, the cannula 90 is shown to have the configuration of a bent tube with a myocardial interface 91 on one end and a connector 92 on the opposing end. In some embodiments of the device, the cannula 90 contacts the locking stem 84 of the apical ring 80. In such embodiments, the cannula 90 may lock into position in the apical ring 80 by any of a number of suitable mechanisms. In some embodiments, the cannula 90 may be tapered such that as it advances into the ventricle 9, the increasing width of the cannula 90 eventually contacts the locking stem 84 of the apical ring 80. This may allow the cannula 90 to lock into place on the apical ring 80. The cannula may be sized and configured to seal with the cannulation apparatus 10 and with the inflow conduit (not shown) to provide for adequate de-airing.

Referring now to FIGS. 7A through 7K, an alternative embodiment of the remote cannulation apparatus and method of remotely coring and cannulating a body part is provided. In this embodiment of the apparatus and method, the coring may be accomplished from the inside of the heart 8 moving outwardly. Cannula attachment mechanisms such as the apical ring 80 of FIG. 3 have been omitted, as in FIGS. 4-5, for clarity.

Figure 7A:
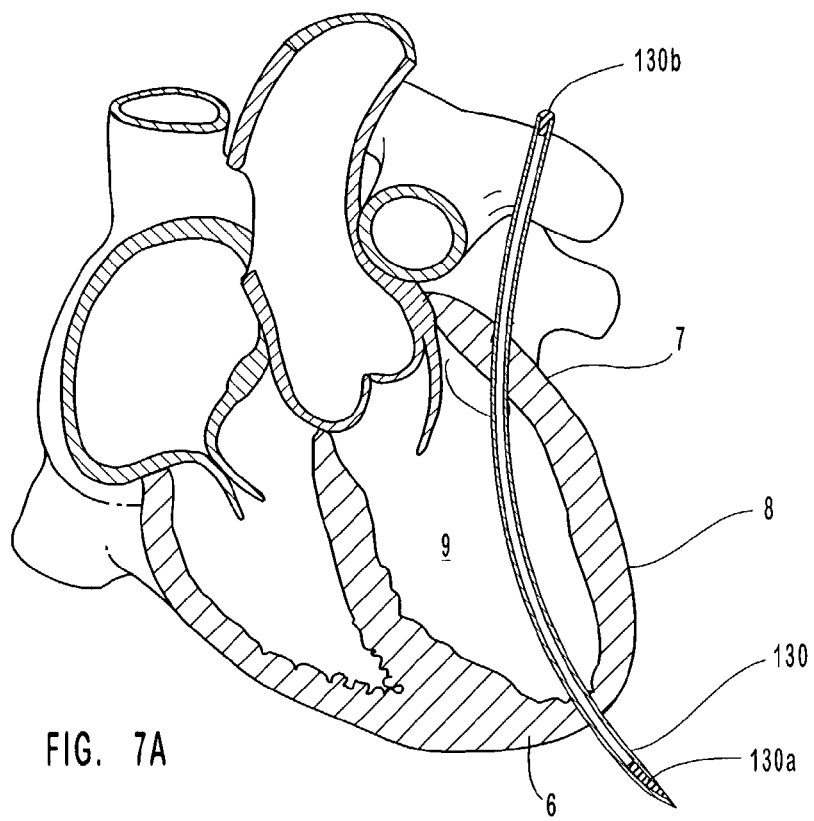
FIG. 7A is a cross-sectional view of a heart and of a sealed hollow trocar used with an alternate embodiment of the remote cannulation assembly in a first step of a method for using this alternate embodiment to core and cannulate a heart.

FIG. 7A shows an isolated cross-sectional view of a heart 8 having a left ventricle 9. In this alternative method of the invention, the left ventricle 9 of the heart 8 is first punctured either by stab incision or using a trocar 130. In this method, the trocar 130 may be independent of the remaining portions of the cannulation assembly (not shown), and may further be elongate and curved in shape to allow proper remote penetration of the apex 6 of the ventricle 9. The puncture is made in the free wall 7 of the heart 8 below the atria. In this step, care is taken to avoid damage to internal structures of the heart 8 such as the papillary muscles, chordae tendonae, and mitral valve apparatus.

The trocar 130 may be hollow and open at both ends to permit the passage of a guidewire (not shown) that may be used to direct the placement of the cannulation assembly (not shown). In FIG. 7A, the hollow curved trocar 130 includes seals 130a, 130b which close the trocar during insertion into the patient. The trocar 130 may additionally include pressure-monitoring apparatus or other components including apertures, to aid in proper placement and guidance of the trocar 130 in use. In the method of the invention, all such apparatus, including the apertures 130a, 130b of the trocar 130 must be sealed during the penetration of the free wall 7 and apex 6 to prevent the introduction of air emboli into the left ventricle 9. This may be ensured using transesophogeal echocardiology.

Following the puncture of the free wall 7 of the left ventricle 9, the curved trocar 130 is passed completely through the volume of the left ventricle 9 and brought into contact with the inside face of the apex 6 of the ventricle 9. Following this, the apex 6 is penetrated by the trocar 130 at the approximate point at which it is desired to insert the cannula (not shown).

Figure 7B:
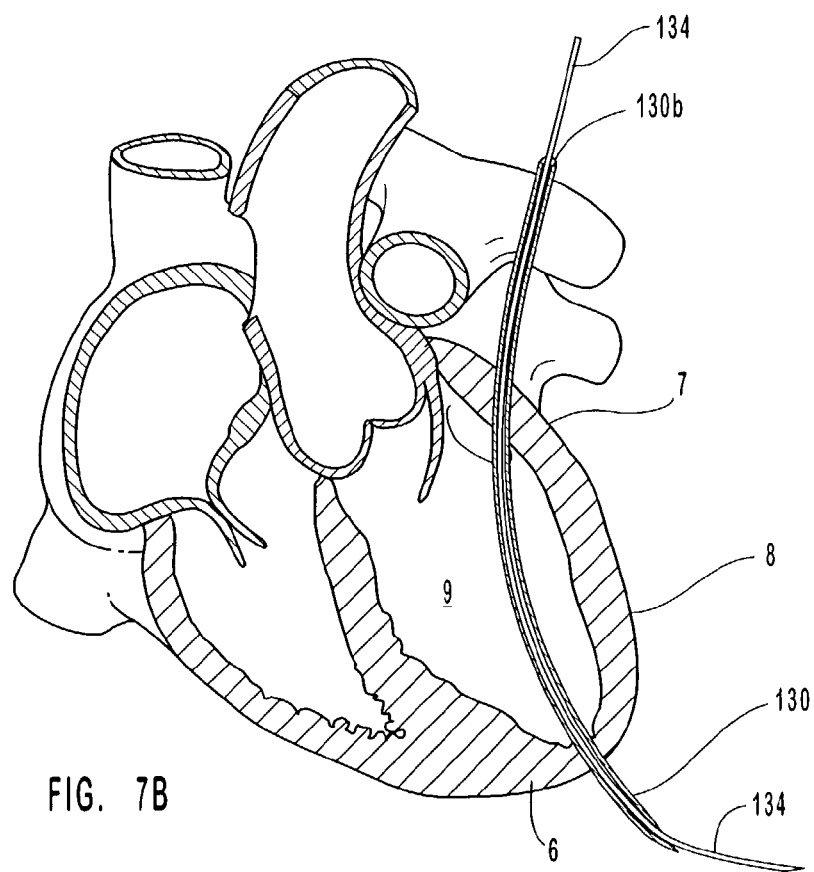
FIG. 7B is a cross-sectional view of a heart, a trocar placed through the heart, and a guidewire placed through the hollow trocar.
Figure 7C:
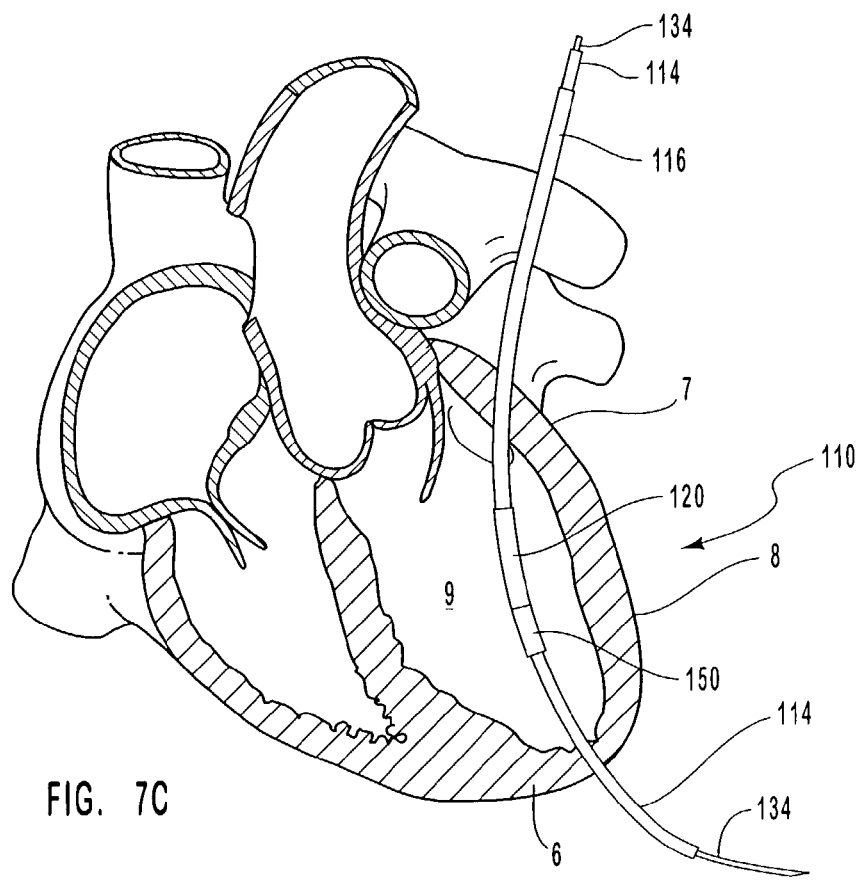
FIG. 7C is a perspective view of an endoscopic cannulation device of the invention placed in a heart (shown in cross-section) along a guidewire.
Figure 7D:
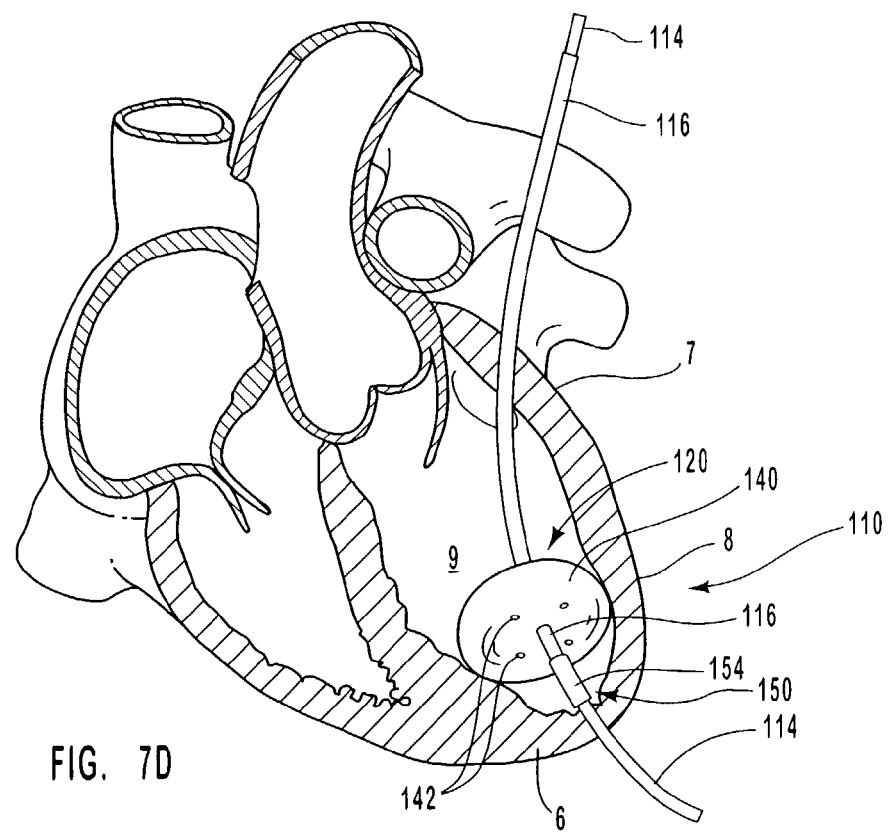
FIG. 7D is a perspective view of the endoscopic cannulation device of FIG. 7C shown with the occlusive device of the fluid stasis assembly deployed.

Referring now to FIG. 7B, after the penetration of the left ventricle 9 by the trocar 130, a guidewire 134 is passed through the interior of the hollow trocar 130 and the seals 130a, 130b such that it travels completely through the interior of the left ventricle 9. Following the threading of the guidewire 134, the trocar 130 may be removed. In FIG. 7C, the trocar 130 has been removed from the heart 8, leaving the guidewire 134 in place. FIG. 7C further shows the remote cannulation assembly 110 of the invention threaded into place in the ventricle 9 by sliding it along the guidewire 134. Following placement of the cannulation apparatus 110 in the heart 8, the guidewire 134 may be removed, as shown in FIG. 7D. Returning to FIG. 7C, the cannulation assembly 110 comprises a shaft 114, a fluid stasis assembly 120, and a coring assembly 150. The remote cannulation assembly 110 may further include a secondary shaft 116. The individual shafts 114, 116 may be used to allow independent control of the fluid stasis assembly 120 and the coring assembly 150. In some embodiments, one or both of the shafts 114, 116 may be rotatable. This property may be utilized to drive the coring assembly 150. In one embodiment of the cannulation assembly 110, the fluid stasis assembly 120 is attached to shaft 116, and the coring assembly is attached to shaft 114, which is configured to rotate.

In FIG. 7D, the fluid stasis assembly 120 is shown to include an occlusive device 140 which is next deployed to create a closed system in the apex 6 of the ventricle 9. This prevents flow of fluid into or out of the apex 6 region of the heart 8, thus allowing coring to proceed without risking exposure of the bloodstream to air and particulates. In FIG. 7D, the occlusive device is shown to be an inflatable balloon occlusive device 140. The occlusive device 140 has a deployed configuration and a stowed configuration. Alternative devices suitable for such use include many which may be stowed in a configuration for positioning inside or outside of a body part, and then deployed on demand. When deployed, such occlusive devices may be configured to generally adopt a shape and/or size which may be utilized to prevent fluid and gas flow past the device. Suitable occlusive devices include inflatable balloons, umbrella-shaped occlusive devices, disk-shaped occlusive devices, and resorbable occlusive structures.

According to the invention, the occlusive devices used provide a seal by being drawn or pressed against the tissue of the body part.

In use, the occlusive device 140 may be mounted such that it may be advanced and retracted along a length of the shaft 116. In some embodiments, the occlusive device may be mounted directly to the shaft 116. In others, the occlusive device 140 may be attached to an intervening slidable mount (not shown). This allows for proper initial placement and inflation of the occlusive device 140 within the heart 8. It also allows for later placement of pressure or tension on the occlusive device 140 to assure the creation of a seal with the wall 7 of the heart 8.

The occlusive device 140 may additionally comprise at least one de-airing port 142 on the surface that faces the wall 7 of the heart 8 where the core will be removed. In this configuration of the remote cannulation apparatus 110, such ports assist in de-airing the sealed portion of the heart prior to removal of the occlusive device 140. This de-airing may include the pumping of saline solution, blood, plasma, artificial blood substitute, Ringer's solution, or other suitable solution through the de-airing ports of the occlusive device 140 into the apex 6 of the heart 8. These ports may be simple apertures opening into the occlusive device and allowing flow of the fluid used to inflate the occlusive device into the body part. Alternatively, the ports 142 may instead be continuous with the shaft 116 such that a fluid passed through the shaft 116 may be emitted from the ports 142. The ports 142 may additionally include valves to prevent backflow of fluid, or alternatively, may be configured to allow removal of fluid from the system.

FIG. 7D also shows the coring assembly 150, attached about the shaft 114, here shown in its compact, stowed configuration. In some embodiments, the coring assembly 150 may also be attached to shaft 116 to aid in withdrawal of the sheath 154 of the coring assembly 150 during its deployment.

Figure 7E:
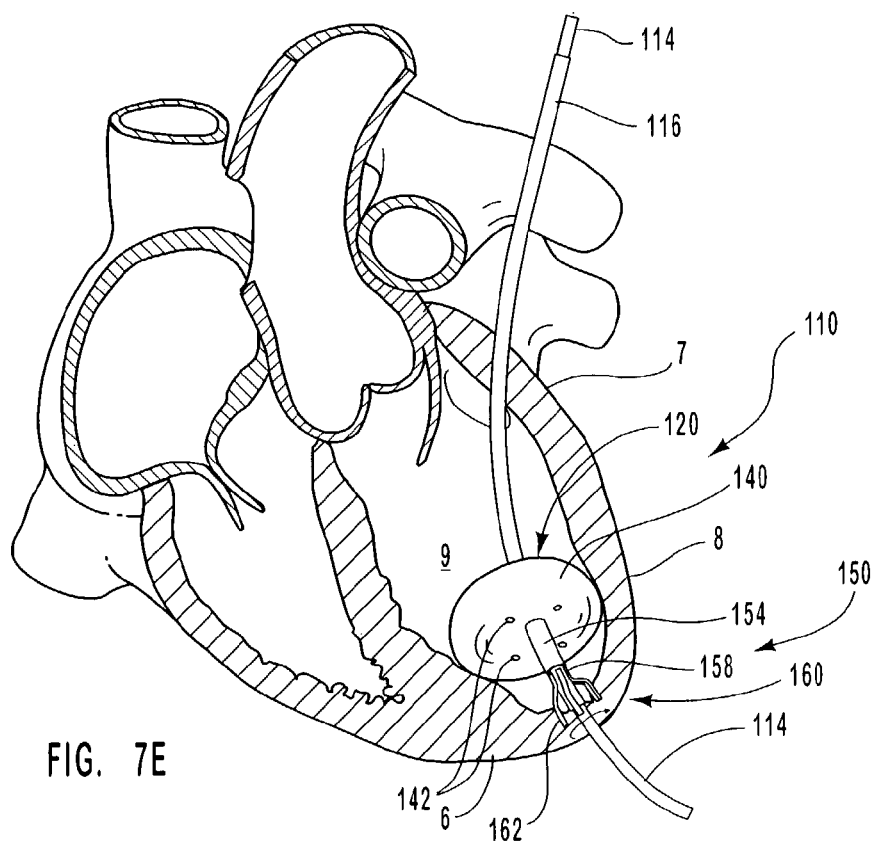
FIG. 7E is a perspective view of the endoscopic cannulation device of FIG. 7C with the occlusive device and the coring assembly deployed, the coring assembly shown coring the heart.

In the next step of the cannulation method of the invention, illustrated in FIG. 7E, the coring assembly 150 is deployed. In this embodiment, deployment is effected by withdrawing the sheath 154, exposing the blade 160 with cutting assembly base 158 and blades 162. In this embodiment of the coring assembly 150, the blade 160 is a rotatable cutting blade including blades 162, which are configured to cut a body part as they are rotated through the body part. The blade is driven by a rotatable shaft 114, which is positioned within the shaft 116. FIG. 7E shows the blade 60 beginning to be progressed through the apex 6 of the heart 8.

Figure 7F:
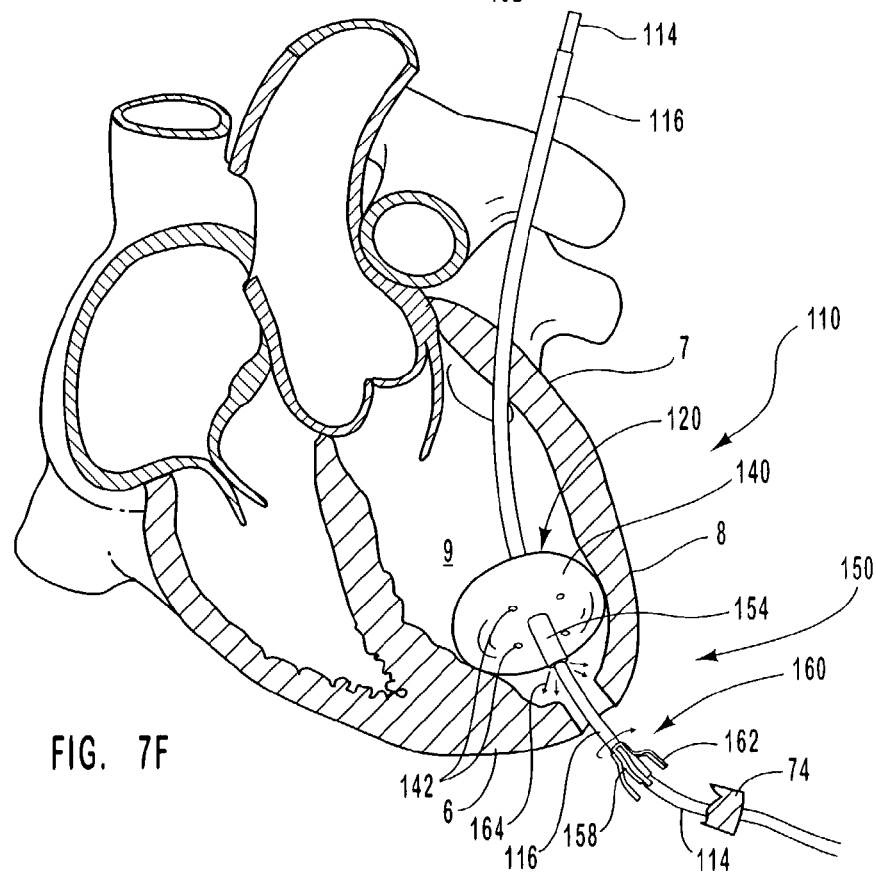
FIG. 7F is a perspective view of the endoscopic cannulation device of FIG. 7E shown having cored through the heart.
Figure 7G:
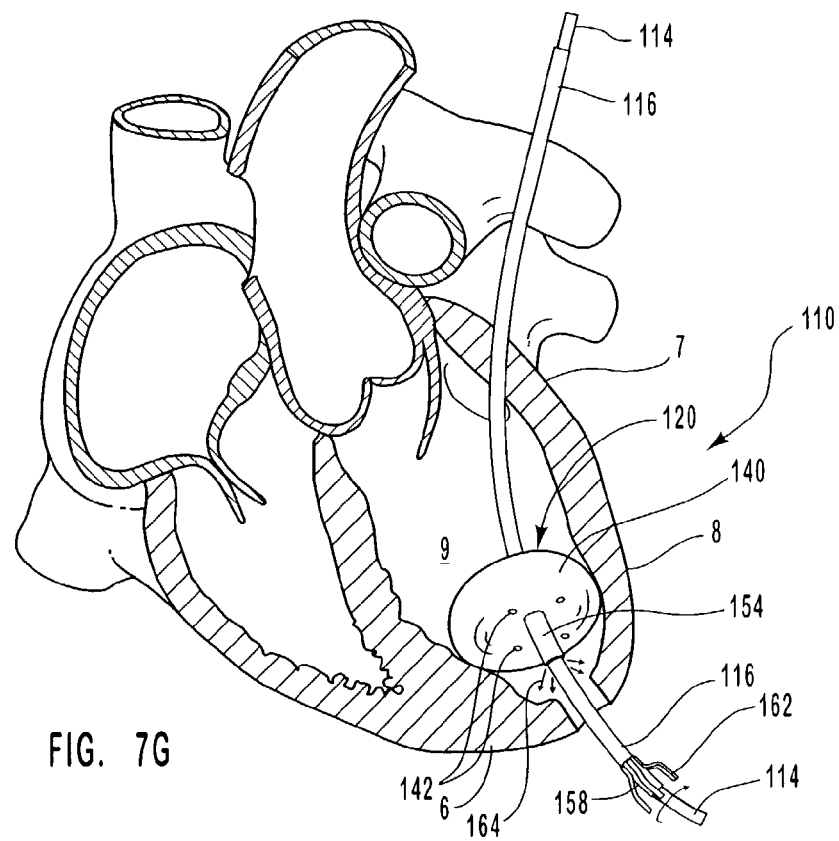
FIG. 7G is a perspective view of the endoscopic cannulation device of FIG. 7F shown during a de-airing step of the coring and cannulation method.

Referring now to FIG. 7F, the coring step of the method is shown completed, in that the blade 60 has cored completely through the apex 6. In this embodiment of the invention, due to the inside-coring-out orientation of the cannulation assembly 110, the coring assembly 150 may omit a core retainer, instead simply pushing the core 74 out of the heart 8 once completely cut. The core 74 will generally remain associated with the shaft 114, allowing it to be easily removed. Specifically, the core 74 may be removed from the body through the incision made for the insertion of the pump or ventricular assist device (not shown). In alternative embodiments of the cannulation apparatus 110, the coring assembly 150 may include a core retainer similar to that discussed earlier and illustrated in FIGS. 1 through 6. Such a core retainer would function generally as previously discussed, by retaining the core 74, allowing it to be withdrawn with the coring assembly 150 out of the body. External removal of the core 74 may make the overall cannulation apparatus 110 less complicated.

In an alternate embodiment, the apex 6 can be cored from the external surface by means of a circular knife through the same abdominal incision used for insertion of the pump, while being used in conjunction with the hemostasis assembly 120. Such a circular knife is similar to the cylindrical coring devices discussed above, but may be wielded manually and directly. This could further reduce the complexity of the current endoscopic device 110 as a whole.

Following the coring of the body part, the apex 6 of the heart 8 may be de-aired and flushed with saline 164 or other physiologically-acceptable fluid such as, but not limited to blood, plasma, artificial blood substitutes, Ringer's solution, or other compounds known in the art. In some embodiments, this fluid may be introduced through de-airing ports 168 positioned in the flexible shaft 114, or the shaft 116, as well as through the ports 142 of the occlusive device 142. Flushing the apex 6 of the ventricle 9 allows mural thrombus and other debris to be removed from the ventricle 9.

Figure 7H:
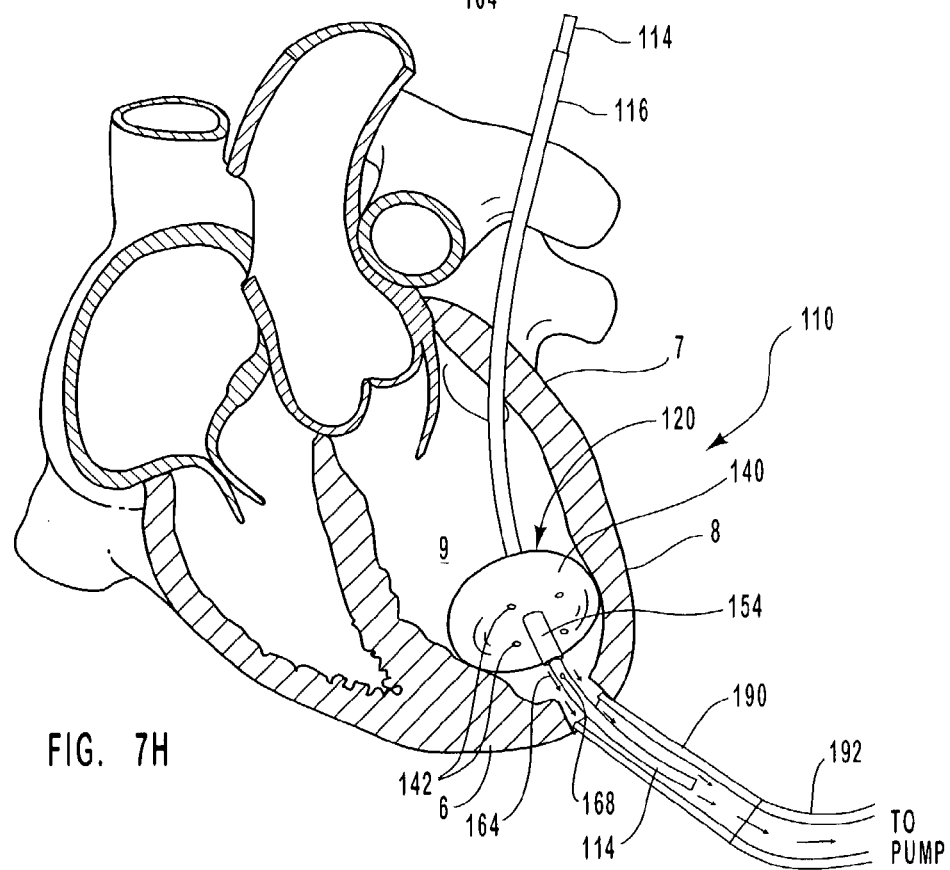
FIG. 7H is a perspective view of the endoscopic cannulation device of FIG. 7F shown during the cannulation step of the method.

Referring to FIGS. 7H and 7I, once the core 74 and coring assembly 150 have been removed or retracted, the cannula 190 can be inserted. At this point, the cannula 190 may be attached to the pump or to an inflow conduit to the pump (not shown), and the pump may, in turn, be attached to the outflow conduit (not shown) to create a closed system after attachment. As the cannula 190 is inserted, saline 164 is infused, filling the lower volume of the ventricle 9, the cannula 190, and the pump (not shown). This helps de-air the ventricle 9, cannula 190, and pump (not shown), as well as the pump outflow conduit (not shown). During this step, the occlusive device 140 is retained in place in the ventricle 9 to maintain a closed system. As a result of the seal affected by the occlusive device 140, the pump may be run at low speeds to complete the de-airing process.

Figure 7K:
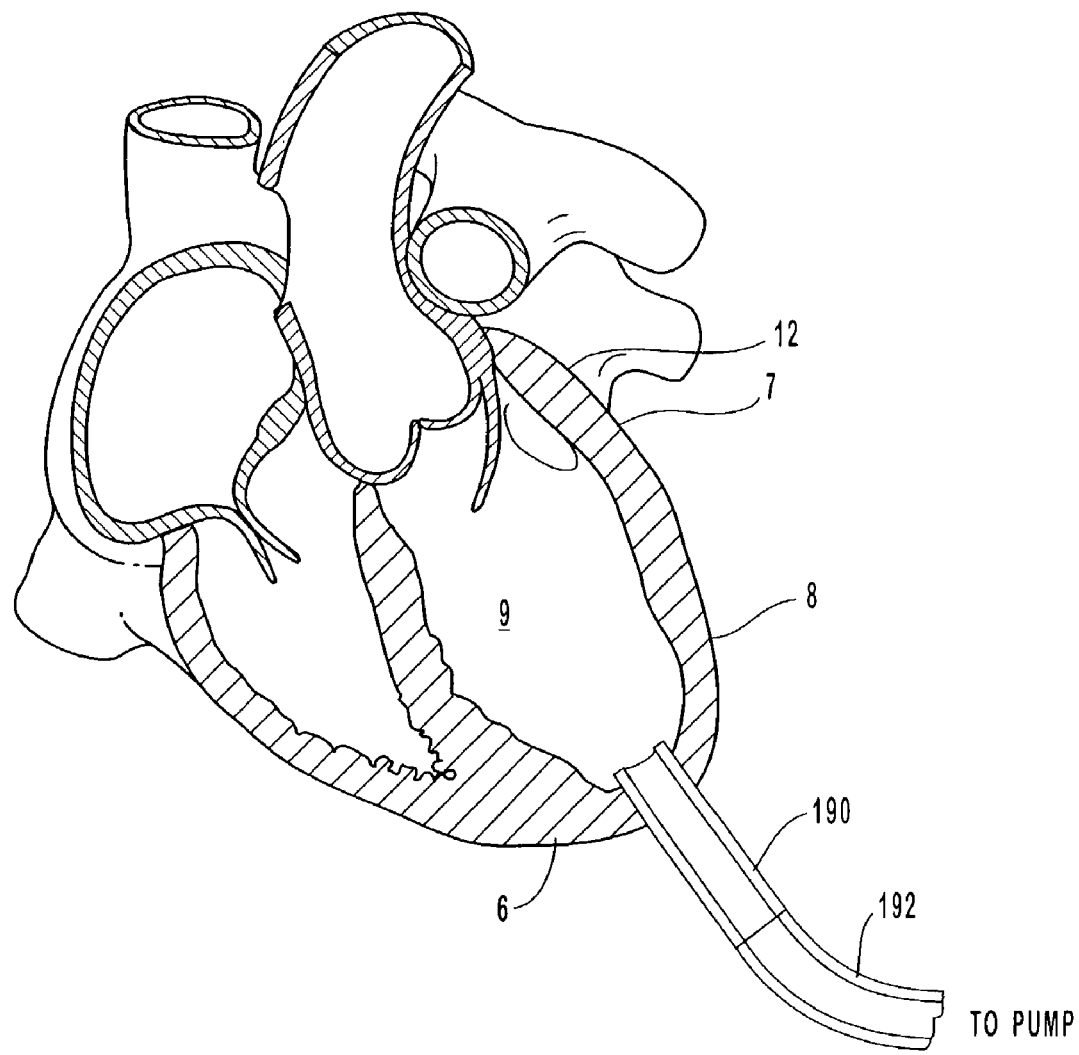
FIG. 7K is a cross-sectional view of a heart shown after complete withdrawal of the endoscopic cannulation apparatus from the hear.

Referring to FIGS. 7J and 7K, once the ventricle 9, cannula 190, and pump system (not shown) is de-aired, and the cannula 190 attached to the pump, the occlusive device 140 may be deflated and withdrawn along with the coring assembly 150 with the shaft 166. The shaft 114 may then be withdrawn from the ventricle 9 and the puncture site 12 on the free wall 7 closed with sutures or other suitable means (not shown).

Figure 8:
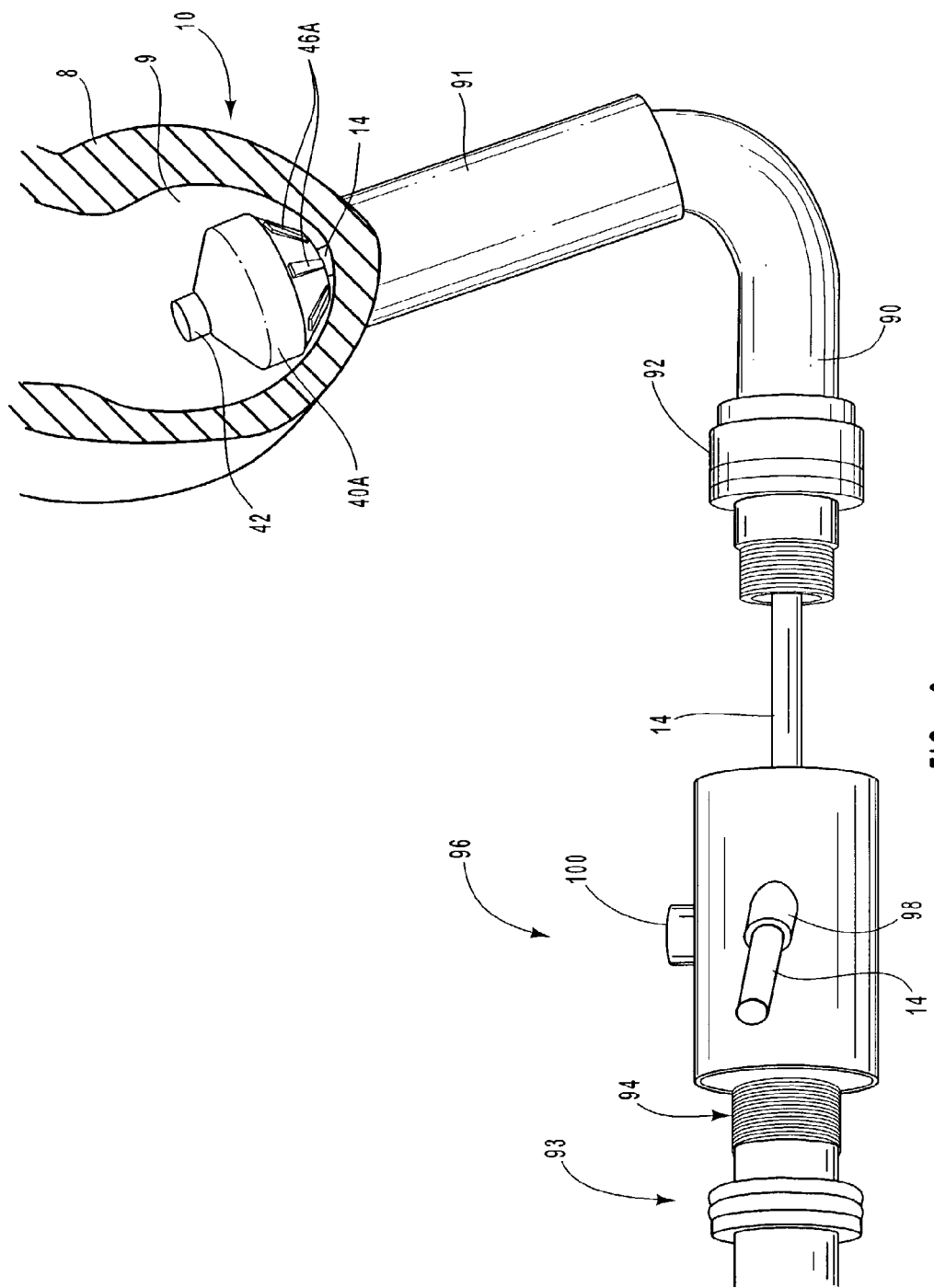
FIG. 8 is a perspective view of an endoscopic cannulation assembly being prepared for a de-airing step of the method of the invention.

Prior to withdrawal of the occlusive device 140, however, the cannula 190 must be attached to the pump system. FIGS. 8 and 9 show the assembly of a de-airing apparatus 96 that may be used to de-air the remainder of the system. This de-airing apparatus 96 is usable with both the first method and apparatus 10 of the invention discussed above and the second method and apparatus 110. Referring now to FIG. 8, after the proper installation of the cannula 90, 190 into the ventricle 9 of the heart 8, the cannula 90, 190 and any closed system enclosing the endoscopic cannulation apparatus 10, 110 may be de-aired. De-airing is most readily accomplished if the aortic anastomosis and cross clamping of the outflow conduit (not shown) has already taken place and if the pump and its accompanying conduits have been placed, thus creating a closed system. This allows for complete de-airing by flooding both the pump and the remainder of the conduits, including the inflow cannula, with a physiologically acceptable fluid such as saline, blood, plasma, artificial blood substitutes, Ringer's solution, or other compounds know in the art.

The aortic anastomosis may be performed using any of the common anastomotic techniques known in the art. Minimally invasive methods are desirable, however, in the methods of the invention. Following this, the outflow conduit running from the pump to the circulatory system may be de-aired by allowing reverse blood flow through the outflow conduit as the aortic wall is unclamped. Air may be removed from the system by withdrawing it using a syringe or other similar sealable means in cooperation with the de-airing port 100 of the de-airing apparatus 96.

In the de-airing step of the method, the de-airing apparatus 96 is assembled about an end of the apparatus 10. In some embodiments, the de-airing apparatus 96 is threaded into place along the shaft 14, which is passed through an end of the apparatus 96 and then through a shaft withdrawal orifice 98 of the de-airing apparatus 96. Alternatively, the de-airing apparatus 96 may be assembled from two halves which may be sealably attached together about the shaft 14. The de-airing apparatus 96 may be a two-piece clamshell device which may be sealed to facilitate de-airing of the system and to allow attachment of the various components in an air-free environment.

It should be noted that alternative configurations of the de-airing apparatus 96 could be manufactured within the scope of the apparatus and method of the invention. One such alternate configuration could include a flexible "y"-connector in place of the de-airing apparatus 96. Alternatively, an elastic connector could be used which could allow the alignment of the fittings and the coring tool while allowing access to the venting apparatus. Still further, silastic seals could be used over any or all of the fittings to provide a seal to any of the components without requiring the addition of the de-airing apparatus 96. This seal could be similar to that used with the shaft aperture 98, which may be an elastic membrane with a central hole that seals over the shaft 14 as it is drawn through the aperture 98. Indeed, alternate configurations could include any combination of these elements.

The attachment of the de-airing apparatus 96 to the pump inflow conduit 93 and the shaft 14 may be made using an interface such as a screw ring (not shown) to allow a sealed attachment. The shaft 14 of the assembly 10 may be placed through a shaft aperture 98 of the de-airing apparatus 96. The de-airing apparatus 96 also includes a de-airing port 100 through which air may be withdrawn. Air may be withdrawn using a de-airing needle or other venting apparatus placed through the vent port 100. Alternatively, a valve may be placed on the de-airing apparatus 96 to infuse saline or another physiologically acceptable fluid, including those listed above, into the closed system of the apparatus 10. The vent port 100 may also be used to draw a vacuum on the sealed system of the apparatus 10.

After these attachments are made, the assembly may be flooded with de-airing fluid through the hollow endoscopic shaft 14 and a vacuum be drawn through the vent port 100 as necessary to ensure full removal of air. This may alternatively be done using a fluid channel and port positioned on the cannula side of the balloon 40A. The pump of the system may be operated at this point to further assist in removal of air, or to test the system.

After completion of the de-airing step, the fluid stasis assembly 20 is withdrawn from the patient. With the system 10 completely flooded with saline or other suitable fluid, and with all air removed from the system 10, the occlusive balloon 40A can be deflated and removed. During the withdrawal of the balloon 40A, the assembly 10 is maintained free of air by seals (silastic or other) on the shaft aperture 98 as well as the de-airing port 100. Any pump operation at this point may be controlled at low pressures to prevent influx of air on the inflow side of the pump. Vent and shaft port caps (not shown) could be placed over the ports 98, 100 if operation of the pump is necessary. Otherwise, positive pressure from either cardiac function or from the infusion of saline will maintain an air free system. The cannula 90 is then separately linked to the inflow conduit 94 within the de-airing apparatus 94. The implantation of the cannula 90 is then completed by sealing the cannula 90 and pump fittings. In some embodiments, this may require pushing the cannula 90 and pump fittings (not shown) securely together to form a seal. This is generally performed prior to disconnection of the de-airing apparatus 96. This disconnection may simply include separating the halves of the de-airing apparatus 96 and removing them.

The method and apparatus of the invention describe means for affecting a remote or minimally invasive coring and cannulation of a body part. The methods may be used for applications such as the coring and cannulation of the left ventricular apex of the heart. These methods decrease the risk of emboli while potentially reducing the need for cardiopulmonary bypass procedures. These methods may also improve the patient's comfort by minimizing the need for thoracotomy or sternotomy by providing the ability to facilitate device introduction without direct surgical access to the heart.

The invention further provides an endoscopic remote cannulation device that uses an occlusive device to affect fluid stasis and a remote blade to core the body part. A cutter guard may be used to allow for cutting devices to be utilized to core the heart without risk of damage to the occlusive device. The ability to provide this fluid stasis prior to coring the ventricle reduces the risk of the introduction of air emboli and may prevent significant blood loss.

The methods of the invention allow a surgeon to remotely (meaning at a distance from, or without direct access) cannulate the heart or other body part. The method includes fluid stasis, allowing for reduced fluid loss and thus a significantly clearer field of view during the medical procedure. The occlusive device further allows for positive pressurization or application of vacuum on the system to affect air removal.

Additionally, the apparatus of the invention may reduce the number of joints or surface mismatches in the blood conduits by allowing full removal of any valves upon completion of installation. Finally, the apparatus of the invention provides improved flexibility due to the application of endoscopic device technologies. Specifically, this allows for the cutting tool to be directed through a winding or bent path.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by U.S. Letters Patent is:

1. An endoscopic cannulation assembly for remotely cannulating a heart at a cannulation site, the cannulation assembly comprising:
   a trocar;
   an endoscopic shaft for guiding functional components of the cannulation assembly to the cannulation site, the endoscopic shaft defining a distal end, a proximal end, an outside surface between the distal end and the proximal end, and a lumen;
   a fluid stasis assembly concentrically and slidably mounted about the outside surface of the endoscopic shaft, the fluid stasis assembly configured to slide with respect to the endoscopic shaft, the fluid stasis assembly comprises an occlusive device, wherein the occlusive device comprises at least one de-airing port configured to emit fluid to help remove bubbles and debris;
   a coring assembly concentrically and slidably mounted about the outside surface of the endoscopic shaft, the fluid stasis assembly and the coring assembly each being mounted adjacent the outside surface of the endoscopic shaft, the coring assembly being adapted to core the heart, wherein the fluid stasis assembly is capable of being deployed prior to or concurrent with operation of the coring assembly;

a core retainer positioned on the coring assembly or the endoscopic shaft for retaining the core that is cut from the heart;

a guard situated between the occlusive device and the coring assembly to protect the occlusive device from contact with the coring assembly; and a cannula sized and configured to insert into the hole formed by the coring assembly to provide a seal to enable de-airing.

2. The endoscopic cannulation assembly of claim 1, wherein the shaft is flexible.

3. The endoscopic cannulation assembly of claim 1, wherein the occlusive device is an inflatable occlusive balloon.

4. The endoscopic cannulation assembly of claim 1, wherein the occlusive device is an expandable umbrella structure.

5. The endoscopic cannulation assembly of claim 1, wherein the occlusive device is an occlusive disk.

6. The endoscopic cannulation assembly of claim 1, wherein the occlusive device is a resorbable occlusive structure.

7. The endoscopic cannulation assembly of claim 6, wherein the resorbable occlusive structure comprises a compound selected from the group consisting of gelatin, polyethylene glycol, hyaluronic acid, polylactic acid, and collagen.

8. The endoscopic cannulation assembly of claim 1, wherein the guard comprises thickened regions of the occlusive device.

9. The endoscopic cannulation assembly of claim 1, wherein the guard comprises protective ridges attached to the occlusive device.

10. The endoscopic cannulation assembly of claim 1, wherein the guard comprises protective overlays attached to the occlusive device.

11. The endoscopic cannulation assembly of claim 1, wherein the guard comprises a protective shield positioned between the fluid stasis assembly and the coring assembly.

12. The endoscopic cannulation assembly of claim 1, wherein the coring assembly comprises a blade.

13. The endoscopic cannulation assembly of claim 12, wherein the blade is a spring-deployed blade.

14. The endoscopic cannulation assembly of claim 12, wherein the blade is a cylindrical cutting tool.

15. The endoscopic cannulation assembly of claim 12, wherein the blade is an elastic cylindrical cutting tool.

16. The endoscopic cannulation assembly of claim 12, wherein the blade is a hydrojet cutter.

17. The endoscopic cannulation assembly of claim 12, wherein the blade is a separate manual blade.

18. The endoscopic cannulation assembly of claim 12, wherein the coring assembly further comprises a blade sheath.

19. The endoscopic cannulation assembly of claim 1, wherein the core retainer is positioned on the coring assembly or shaft and is a raised ridge.

20. The endoscopic cannulation assembly of claim 1, wherein the core retainer is positioned on the coring assembly or shaft and is a raised helical ridge.

21. The endoscopic cannulation assembly of claim 1, wherein the core retainer is positioned on the coring assembly or shaft and is a barb.

22. The endoscopic cannulation assembly of claim 1, wherein the core retainer is positioned on the coring assembly or shaft and is a hook.

23. An endoscopic cannulation assembly for remotely cannulating a heart at a cannulation site, the cannulation assembly comprising:

a trocar mounted to an endoscopic shaft for guiding functional components of the cannulation assembly to the cannulation site, the endoscopic shaft defining a distal end, a proximal end, and an outside surface between the distal end and the proximal end;

a fluid stasis assembly concentrically and slidably mounted about the outside surface of the endoscopic shaft, the fluid stasis assembly including an occlusive device having a stowed configuration and a deployed configuration, the occlusive device further comprises at least one de-airing port configured to emit fluid to help remove bubbles and debris, the fluid stasis assembly configured to slide with respect to the shaft;

a coring assembly concentrically and slidably mounted about the outside surface of the endoscopic shaft, the fluid stasis assembly and the coring assembly each being mounted adjacent the outside surface of the endoscopic shaft, the coring assembly including a blade that may be deployed to cut and remove a core from the heart, wherein the fluid stasis assembly is capable of being deployed prior to or concurrent with operation of the coring assembly;

a core retainer positioned on the coring assembly or the endoscopic shaft for retaining the core that is cut from the heart;

a guard situated between the occlusive device and the coring assembly to protect the occlusive device from contact with the coring assembly; and a cannula sized and configured to insert into the hole formed by the coring assembly to provide a seal to enable de-airing.

24. The endoscopic cannulation assembly of claim 23, wherein the endoscopic shaft is flexible.

25. The endoscopic cannulation assembly of claim 23, wherein the endoscopic shaft includes more than one endoscopic shaft to allow independent control of individual elements of the cannulation assembly.

26. The endoscopic cannulation assembly of claim 23, wherein the occlusive device of the fluid stasis assembly is an inflatable occlusive balloon.

27. The endoscopic cannulation assembly of claim 23, wherein the occlusive device of the fluid stasis assembly is an expandable umbrella structure.

28. The endoscopic cannulation assembly of claim 23, wherein the occlusive device of the fluid stasis assembly is a resorbable occlusive structure.

29. The endoscopic cannulation assembly of claim 28, wherein the resorbable occlusive structure comprises a compound selected from the group consisting of gelatin, polyethylene glycol, hyaluronic acid, polylactic acid, and collagen.

30. The endoscopic cannulation assembly of claim 23, wherein the blade is a separate manual blade.

31. The endoscopic cannulation assembly of claim 23, wherein the blade is a spring-deployed blade.

32. The endoscopic cannulation assembly of claim 31, wherein the coring assembly further comprises a sheath.

33. The endoscopic cannulation assembly of claim 23, wherein the core retainer comprises a helical ridge positioned on the coring assembly.

34. The endoscopic cannulation assembly of claim 23, wherein the coring assembly comprises an elastic cylindrical cutting tool and a core retainer.

35. The endoscopic cannulation assembly of claim 34, wherein the core retainer comprises a helical ridge positioned on the coring assembly.

36. The endoscopic cannulation assembly of claim 34, wherein the core retainer comprises a helical ridge positioned on an inside face of the elastic cylindrical coring tool.

37. The endoscopic cannulation assembly of claim 23, wherein the coring assembly comprises a hydrojet cutter and a core retainer.

38. The endoscopic cannulation assembly of claim 37, wherein the core retainer comprises a helical ridge positioned on the coring assembly.

39. The endoscopic cannulation assembly of claim 23, wherein the guard is attached to the occlusive device to prevent damage to the occlusive device from the coring assembly.

40. The endoscopic cannulation assembly of claim 39, wherein the guard comprises a thickened region of the occlusive device.

41. The endoscopic cannulation assembly of claim 39, wherein the guard comprises a protective ridge attached to the occlusive device.

42. The endoscopic cannulation assembly of claim 39, wherein the guard comprises protective overlays attached to the occlusive device.

43. The endoscopic cannulation assembly of claim 39, wherein the guard comprises protective shields positioned between the fluid stasis assembly and the coring assembly.

44. An endoscopic cannulation assembly for remotely cannulating a heart at a cannulation site, the cannulation assembly comprising:
  a hollow trocar for penetrating the heart, wherein the trocar is mounted to an endoscopic shaft for guiding functional components of the cannulation assembly to the cannulation site, the endoscopic shaft defining a distal end, a proximal end, and an outside surface between the distal end and the proximal end;
  a guidewire passing through the trocar;
  the endoscopic shaft configured to slide along the guidewire into the heart;
  a coring assembly concentrically and slidably mounted about the outside surface of the endoscopic shaft, the coring assembly including a blade for cutting and removing a core from the heart;
  a fluid stasis assembly concentrically and slidably mounted about the outside surface of the endoscopic shaft, the coring assembly and the fluid stasis assembly are each mounted adjacent the outside surface of the endoscopic shaft, the fluid stasis assembly comprising an occlusive device for creating a seal with the heart, wherein the occlusive device further comprises at least one de-airing port configured to emit fluid to help remove bubbles and debris, wherein the fluid stasis assembly is capable of being deployed prior to or concurrent with operation of the coring assembly, the fluid stasis assembly configured to slide with respect to the shaft;
  a guard situated between the occlusive device and the coring assembly to protect the occlusive device from contact with the coring assembly; and
  a cannula sized and configured to insert into the hole formed by the coring assembly to provide a seal to enable de-airing.

45. The endoscopic cannulation assembly of claim 44, wherein the shaft is flexible.

46. The endoscopic cannulation assembly of claim 44, wherein the occlusive device is an inflatable occlusive balloon.

47. The endoscopic cannulation assembly of claim 44, wherein the occlusive device is an expandable umbrella structure.

48. The endoscopic cannulation assembly of claim 44, wherein the occlusive device is an occlusive disk.

49. The endoscopic cannulation assembly of claim 44, wherein the occlusive device is a resorbable occlusive structure.

50. The endoscopic cannulation assembly of claim 49, wherein the resorbable occlusive structure comprises a compound selected from the group consisting of gelatin, polyethylene glycol, hyaluronic acid, polylactic acid, and collagen.

51. The endoscopic cannulation assembly of claim 44, wherein the blade is a spring-deployed blade.

52. The endoscopic cannulation assembly of claim 44, wherein the blade is a cylindrical cutting tool.

53. The endoscopic cannulation assembly of claim 44, wherein the blade is an elastic cylindrical cutting tool.

54. The endoscopic cannulation assembly of claim 44, wherein the blade is a hydrojet cutter.

55. The endoscopic cannulation assembly of claim 44, wherein the blade is a separate manual blade.

56. The endoscopic cannulation assembly of claim 44, wherein the blade further includes a blade sheath.

57. The endoscopic cannulation assembly of claim 56, wherein the blade is a resilient member maintained in a retracted configuration within the sheath that expands during deployment and which returns to its deployed configuration upon retraction of the sheath.

58. The endoscopic cannulation assembly of claim 44, wherein the coring assembly further includes a core retainer.

59. The endoscopic cannulation assembly of claim 58, wherein the core retainer is a raised ridge.

60. The endoscopic cannulation assembly of claim 58, wherein the core retainer is a raised helical ridge.

61. The endoscopic cannulation assembly of claim 58, wherein the core retainer comprises a barb.

62. The endoscopic cannulation assembly of claim 58, wherein the core retainer comprises a hook.

63. The endoscopic cannulation assembly of claim 58, wherein the core retainer comprises a helical ridge positioned on the coring assembly to engage the core cut from the body part to allow its withdrawal from the body.

64. The endoscopic cannulation assembly of claim 1, wherein the fluid stasis assembly is mounted toward the distal end of the endoscopic shaft relative to the coring assembly, and wherein the coring assembly is mounted toward the proximal end of the endoscopic shaft relative to the fluid stasis assembly.

65. The endoscopic cannulation assembly of claim 23, wherein the fluid stasis assembly is mounted toward the distal end of the endoscopic shaft relative to the coring assembly, and wherein the coring assembly is mounted toward the proximal end of the endoscopic shaft relative to the fluid stasis assembly.

66. The endoscopic cannulation assembly of claim 44, wherein the fluid stasis assembly is mounted toward the distal end of the endoscopic shaft relative to the coring assembly, and wherein the coring assembly is mounted toward the proximal end of the endoscopic shaft relative to the fluid stasis assembly.

* * * * *